(12) United States Patent
Oh et al.

(10) Patent No.: US 9,408,585 B2
(45) Date of Patent: Aug. 9, 2016

(54) X-RAY IMAGING APPARATUS AND CONTROL METHOD FOR THE SAME

(71) Applicants: SAMSUNG ELECTRONICS CO., LTD., Suwon-si (KR); Commonwealth Scientific and Industrial Research Organisation, Campbell, ACT (AU)

(72) Inventors: Hyun Hwa Oh, Hwaseong-si (KR); Sung Hoon Kang, Suwon-si (KR); Young Hun Sung, Hwaseong-si (KR); Andrew Wesley Stevenson, Clayton (AU); Stephen William Wilkins, Clayton (AU); Timur Eugenievich Gureyev, Clayton (AU); Yakov Nesterets, Clayton (AU)

(73) Assignees: SAMSUNG ELECTRONICS CO., LTD., Suwon-si (KR); COMMONWEALTH SCIENTIFIC AND INDUSTRIAL RESEARCH ORGANISATION, Campbell (AU)

( * ) Notice: Subject to any disclaimer, the term of this patent is extended or adjusted under 35 U.S.C. 154(b) by 146 days.

(21) Appl. No.: 14/205,671

(22) Filed: Mar. 12, 2014

(65) Prior Publication Data

US 2014/0270064 A1 Sep. 18, 2014

(30) Foreign Application Priority Data

Mar. 12, 2013 (KR) ........................ 10-2013-0026200

(51) Int. Cl.
*A61B 6/06* (2006.01)
*G01N 23/20* (2006.01)
*A61B 6/00* (2006.01)

(52) U.S. Cl.
CPC ................. *A61B 6/482* (2013.01); *A61B 6/484* (2013.01); *A61B 6/502* (2013.01); *A61B 6/5211* (2013.01); *A61B 6/583* (2013.01); *G01N 23/20075* (2013.01); *G01N 2223/6126* (2013.01)

(58) Field of Classification Search
CPC .... A61B 6/484; A61B 6/4291; A61B 6/4441; A61B 6/502; A61B 6/481; A61B 6/4233; A61B 6/504; A61B 6/06; A61B 6/4035; A61B 6/032; A61B 6/4464; A61B 6/4452; A61B 6/482; A61B 6/4021; A61B 6/503; A61B 6/507; A61B 6/583; A61B 6/5211; G01N 2223/6126; G01N 23/20075
USPC ........................................................ 378/53, 62
See application file for complete search history.

(56) References Cited

U.S. PATENT DOCUMENTS

| 6,493,422 | B2 * | 12/2002 | Wilkins | ................. | A61B 6/484 |
| | | | | | 378/98.11 |
| 2004/0264626 | A1 * | 12/2004 | Besson | .................. | A61B 6/508 |
| | | | | | 378/4 |
| 2005/0226376 | A1 * | 10/2005 | Yun | ....................... | G01T 1/2018 |
| | | | | | 378/62 |

(Continued)

FOREIGN PATENT DOCUMENTS

| EP | 2953097 A1 * 12/2015 | ............ G06T 11/005 |
| KR | 10-2010-0094660 A | 8/2010 |

(Continued)

OTHER PUBLICATIONS

Epple, FM, et al., "Unwrapping Differential X-ray Phase Contrast Images Through Phase Estimation from Multiple Energy Data", Dec. 2, 2013, Optics Express, vol. 21, No. 24, pp. 689-693.*

*Primary Examiner* — Anastasia Midkiff
(74) *Attorney, Agent, or Firm* — Sughrue Mion, PLLC

(57) ABSTRACT

The X-ray imaging apparatus to form a phase contrast image includes an X-ray source that generates X-rays to emit the X-rays to an object; an X-ray detector configured to detect X-rays having passed through the object to acquire phase contrast image signals on a per energy band basis; and a quantitative data acquirer configured to calculate approximate quantitative data of two or more constituent substances of the object using a relation between the phase contrast image signals on the per energy band basis and quantitative data of the constituent substances, and estimate quantitative data of the constituent substances by iteratively applying a regularization function to the approximate quantitative data.

19 Claims, 24 Drawing Sheets

(56) References Cited

U.S. PATENT DOCUMENTS

| | | |
|---|---|---|
| 2006/0039532 A1 | 2/2006 | Wu et al. |
| 2009/0128830 A1* | 5/2009 | Kottler ................. G01B 15/025 356/521 |
| 2012/0237104 A1* | 9/2012 | Fouras ..................... A61B 5/08 382/132 |
| 2012/0307970 A1* | 12/2012 | Sommerer ........... G01N 23/046 378/62 |
| 2013/0070062 A1* | 3/2013 | Fouras ............... H04N 13/0203 348/50 |

FOREIGN PATENT DOCUMENTS

| | | | |
|---|---|---|---|
| KR | 10-2011-0079742 A | 7/2011 | |
| KR | 10-2011-0111955 A | 10/2011 | |
| KR | 10-2012-0026908 A | 3/2012 | |
| WO | WO 2013030698 A1 * | 3/2013 | ........... G01N 23/046 |

* cited by examiner

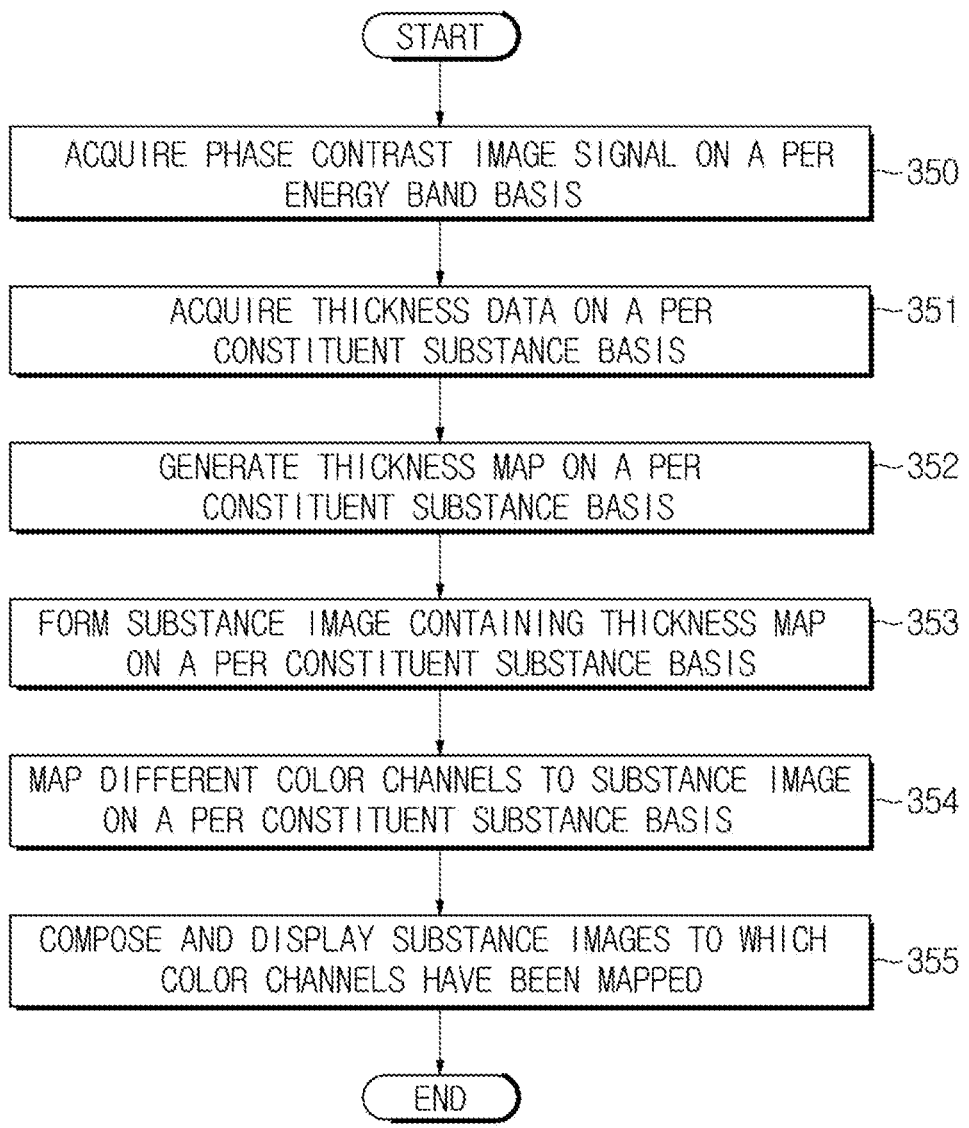

X-RAY IMAGING APPARATUS AND CONTROL METHOD FOR THE SAME

CROSS-REFERENCE TO RELATED APPLICATION

This application claims priority from the Korean Patent Application No. 10-2013-0026200, filed on Mar. 12, 2013, in the Korean Intellectual Property Office, the disclosure of which is incorporated herein by reference in its entirety.

BACKGROUND

1. Field

Apparatuses and methods consistent with exemplary embodiments relate to an X-ray imaging of an object.

2. Description of the Related Art

An X-ray imaging apparatus may form an image of the internal structure of an object by emitting X-rays to the object and detecting X-rays having passed through the object.

Because the attenuation or absorption of X-rays varies according to constituent substances of an object, the internal structure of the object may be imaged by using the intensity of X-rays having passed through the object.

When passing through the object, X-rays undergo refraction and interference due to constituent substances of an object, which causes a phase shift of the X-rays. Such phase shift depends on properties of constituent substances. In recent years, technologies for imaging the interior of an object using phase contrast of X-rays have been developed.

X-rays have a greater phase-shift coefficient than an absorption coefficient on a per substance basis. Therefore, there is a need for methods and apparatuses which enable the acquisition of a high-contrast image with minimal X-ray exposure by using the phase contrast imaging.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments provide an X-ray imaging apparatus which estimates quantitative data regarding an object using phase contrast image signals corresponding to a plurality of different energy bands, and provides a user with the estimated data in various ways, and a control method for the same.

In accordance with an aspect of an exemplary embodiment, there is provided an X-ray imaging apparatus to form a phase contrast image, includes an X-ray source that generates X-rays to emit the X-rays to an object, an X-ray detector that detects X-rays having passed through the object to acquire phase contrast image signals with regard to the object on a per energy band basis, and a quantitative data acquirer that calculates approximate quantitative data regarding two or more constituent substances of the object using a relation between the phase contrast image signals on a per energy band basis and quantitative data regarding the constituent substances, and estimates quantitative data regarding the constituent substances by iteratively applying a regularization function to the approximate quantitative data.

In accordance with an aspect of an exemplary embodiment, there is provided a control method for an X-ray imaging apparatus to form a phase contrast image, includes acquiring phase contrast image signals with regard to an object on a per energy band basis, calculating approximate quantitative data regarding two or more constituent substances of the object using a relation between the phase contrast image signals on a per energy band basis and quantitative data regarding the constituent substances, and estimating quantitative data regarding the constituent substances by iteratively applying a regularization function to the approximate quantitative data.

The quantitative data acquirer may judge whether or not the estimated quantitative data satisfies a preset verification requirement to verify reliability of the estimated quantitative data.

The quantitative data acquirer may acquire the estimated quantitative data as quantitative data regarding the constituent substances if it is judged that the estimated quantitative data satisfies the verification requirement.

The control method for the X-ray imaging apparatus may further include judging whether or not the estimated quantitative data satisfies a preset verification requirement to verify reliability of the estimated quantitative data.

The control method for the X-ray imaging apparatus may further include acquiring the estimated quantitative data as quantitative data regarding the constituent substances if it is judged that the estimated quantitative data satisfies the verification requirement.

The control method for the X-ray imaging apparatus may further include estimating new quantitative data by again applying the regularization function to the estimated quantitative data if it is judged that the estimated quantitative data does not satisfy the verification requirement.

BRIEF DESCRIPTION OF THE DRAWINGS

The above and/or other aspects will become more apparent by describing certain exemplary embodiments, with reference to the accompanying drawings, in which:

FIG. 21 is a flowchart showing generation of a single image involving thickness data on a per constituent substance basis according to an exemplary embodiment.

DETAILED DESCRIPTION

Figure 1:
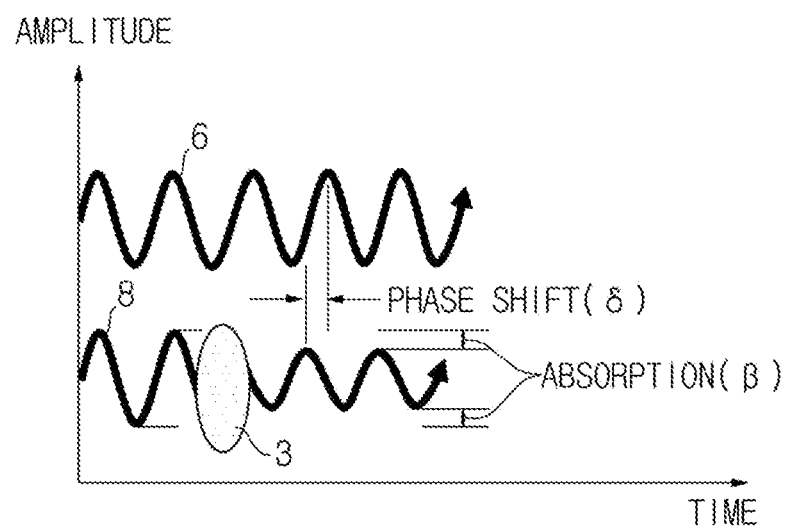
FIG. 1 is a view schematically showing phenomena occurring when X-rays pass through an object.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

FIG. 1 is a view schematically showing phenomena occurring when X-rays pass through an object.

Assuming that the X-rays having both particle and wave properties are electromagnetic X-ray waves 6 and 8, as exemplarily shown in FIG. 1, the X-ray wave 8 undergoes amplitude reduction and phase shift ($\delta$) while passing through an object 3, as compared to the X-ray wave 6. Amplitude reduction of X-rays is caused by absorption ($\beta$) of the X-rays passing through the object. This is referred to as X-ray attenuation.

Figure 2:
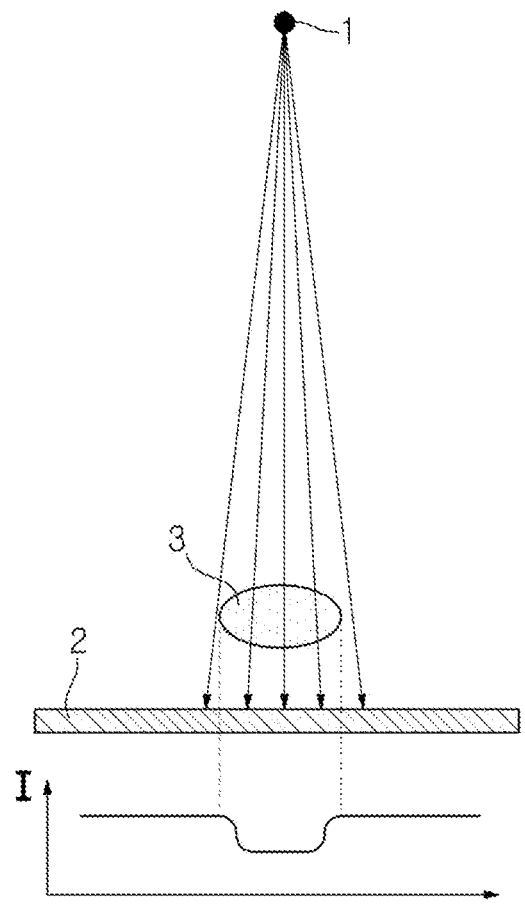
FIG. 2 is a view schematically showing acquisition of an X-ray image using X-ray attenuation.

FIG. 2 is a view schematically showing acquisition of an X-ray image using X-ray attenuation.

Constituent substances of an object exhibit different X-ray attenuation, i.e., different X-ray absorption. In the related art, the interior of an object has been imaged using X-ray attenuation. In the following description of the exemplary embodiments, an image using X-ray attenuation is referred to as an absorptive image. To form the absorptive image, as exemplarily shown in FIG. 2, an X-ray source 1 emits X-rays to an object 3 and an X-ray detector 2, which is located close to the object 3 or comes into contact with the object 3, detects X-rays having passed through the object 3. The intensity of the detected X-rays includes data regarding X-ray attenuation, and thus an absorptive image of the object 3 may be formed using the intensity of X-rays.

Figure 3:
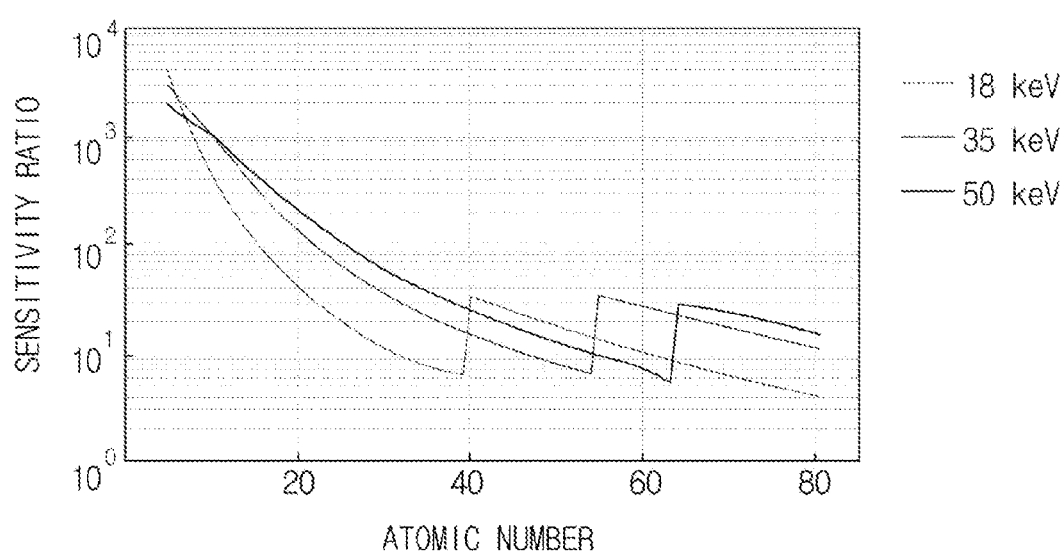
FIG. 3 is a graph showing X-ray attenuation and sensitivity to phase shift.

FIG. 3 is a graph showing X-ray attenuation and sensitivity to phase shift.

Phase shift of X-rays occurs because constituent substances of an object cause refraction and interference of X-rays while X-rays pass through the object. Assuming that the index indicating X-ray attenuation is $\beta$ and the index indicating phase shift of X-rays is $\delta$, a sensitivity ratio of the coefficients ($\delta/\beta$) may be represented as shown in FIG. 3. Referring to FIG. 3, it will be appreciated that phase shift of X-rays is thousands of times more sensitive than X-ray attenuation, although the sensitivity ratio varies according to constituent substances of the object and energy levels of X-rays.

Figure 4A:
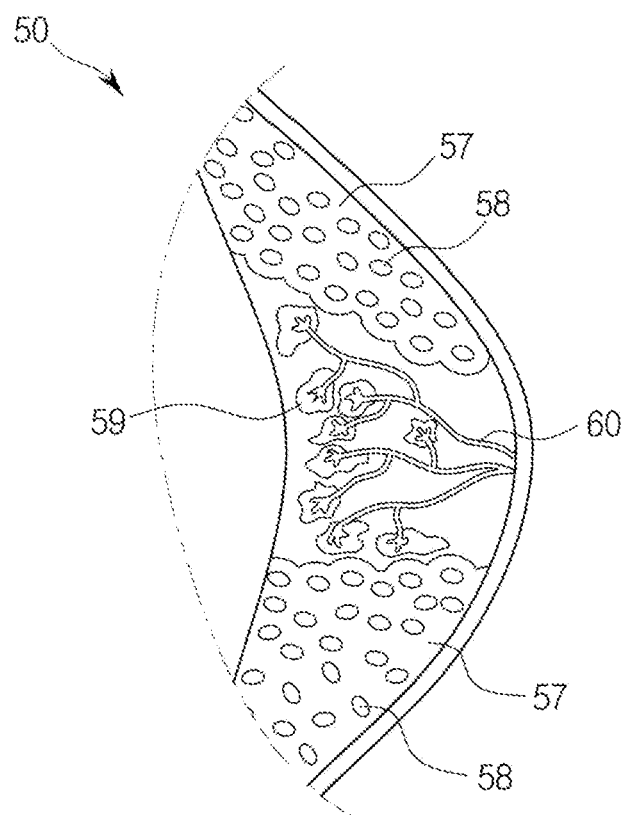
FIG. 4A is a view diagrammatically showing internal constituent substances of the breast.
Figure 4B:
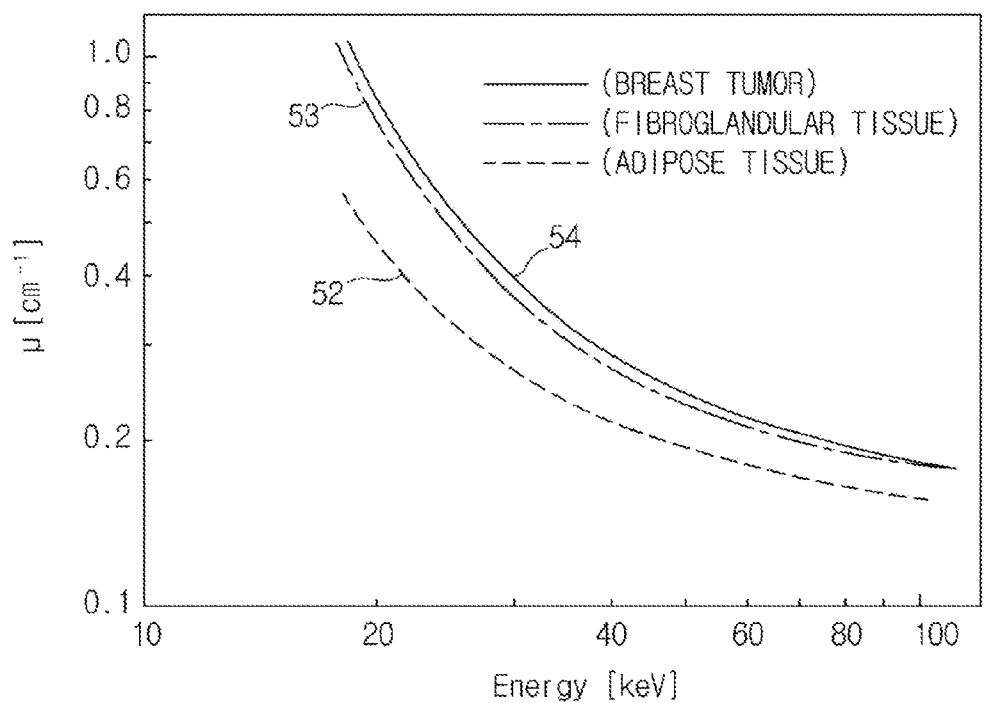
FIG. 4B is a graph showing attenuation coefficients of internal constituent substances of the breast.

FIG. 4A is a view diagrammatically showing internal constituent substances of the breast, and FIG. 4B is a graph showing attenuation coefficients of internal constituent substances of the breast.

For example, tissues of the breast 50 include fibrous tissues 57 constituting the periphery of the breast for shape maintenance, adipose tissues 58 distributed throughout the breast, mammary glands 59 for generation of breast milk, lactiferous ducts 60 as movement passage of breast milk, etc. Of these tissues, the mammary glands 59 and the lactiferous ducts 60, related to generation and supply of breast milk, are referred to as fibroglandular tissues of the breast. FIG. 4B shows attenuation coefficients of internal constituent substances of adipose tissue, fibroglandular tissues, and lesion as graphs 52, 53, and 54, respectively. As exemplarily shown in FIG. 4B, the fibroglandular tissues exhibit an X-ray attenuation coefficient pt similar to that of lesions 54, such as tumors, etc.

In addition, since the breast is composed of soft tissue alone, as exemplarily shown in FIGS. 4A and 4B, internal constituent substances of the breast do not have a great difference in X-ray attenuation. Thus, it may be difficult to acquire accurate data regarding internal constituent substances of the breast from absorptive imaging alone.

As exemplarily shown in FIG. 3, phase shift of X-rays is dozens of times to thousands of times more sensitive than X-ray attenuation. Therefore, with regard to an object having no great difference in X-ray attenuation between constituent substances thereof, such as the breast, acquisition of a more vivid and distinguishable X-ray image may be possible using phase shift of X-rays.

Imaging the interior of an object using the theory that respective constituent substances of an object exhibit different phase shifts of X-rays is referred to as phase contrast imaging, and an image formed via phase contrast imaging is referred to as a phase contrast image.

Such a phase contrast image is formed via interferometry, diffraction-enhanced imaging, in-line phase contrast imaging, and grating interferometry, for example. In particular, in-line phase contrast imaging may be realized via a configuration similar to a general X-ray imaging apparatus without requiring additional optical elements, such as a diffraction lattice or a reflector. The X-ray imaging apparatus according to an exemplary embodiment is devised to acquire a phase contrast image using in-line phase contrast imaging.

Figure 5A:
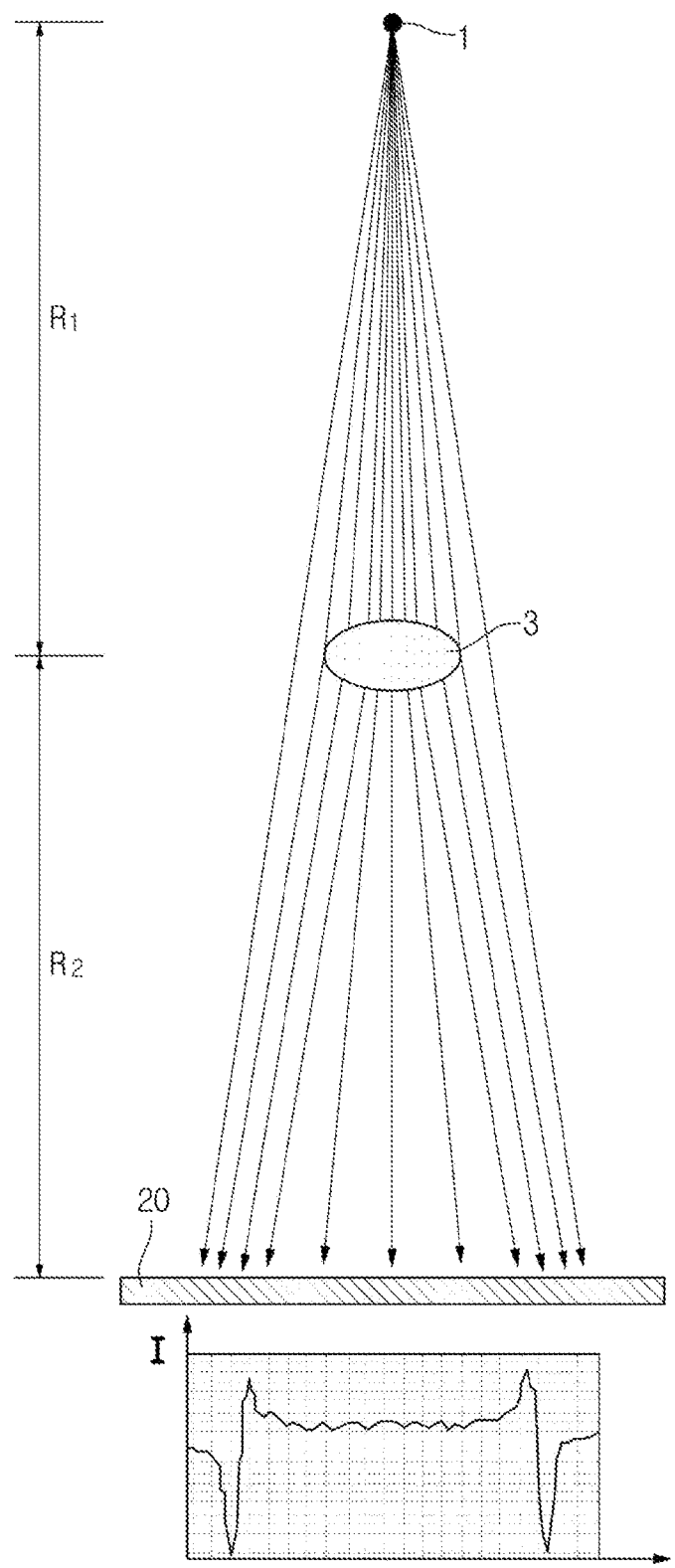
FIG. 5A is a view schematically showing acquisition of a phase contrast image.
Figure 5B:
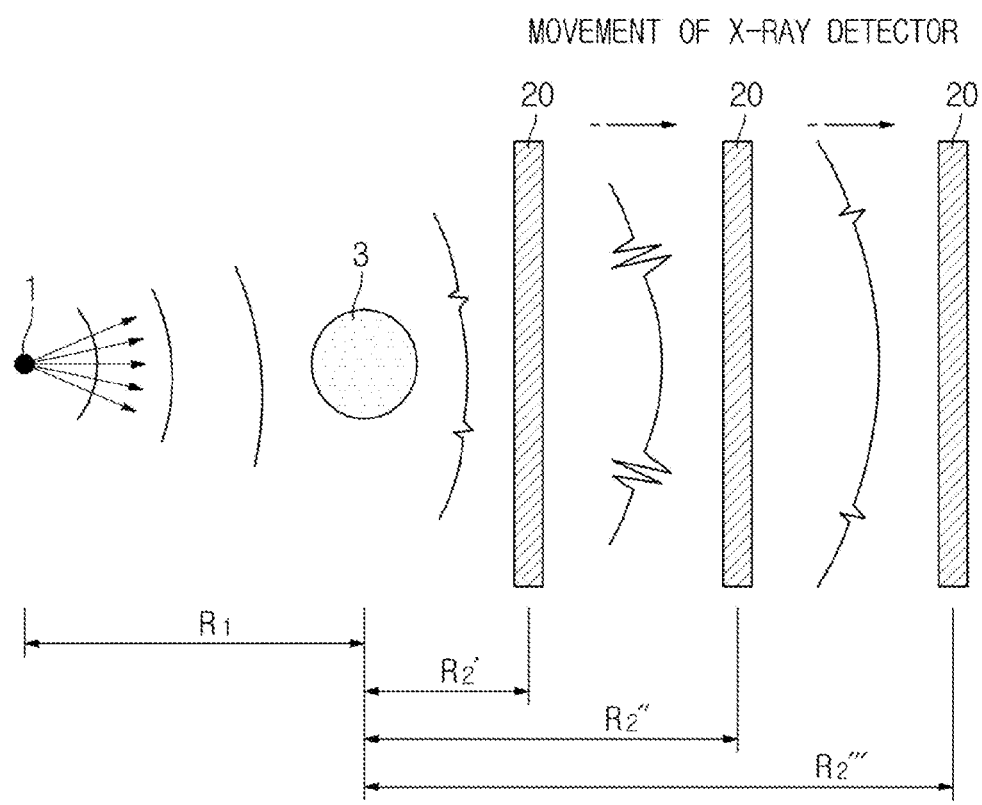
FIG. 5B is a view schematically showing acquisition of a phase contrast image while an X-ray detector is being moved.

FIG. 5A is a view schematically showing acquisition of a phase contrast image, and FIG. 5B is a view schematically showing acquisition of a phase contrast image while an X-ray detector is being moved.

In in-line phase contrast imaging, as exemplarily shown in FIG. 5A, an X-ray detector 20 is spaced from the object 3 by a distance $R_2$, and the object 3 is spaced from an X-ray source 1 by a distance $R_1$. If the X-ray source 1 emits X-rays to the object 3, the emitted X-rays first pass through the object 3 and thereafter are detected by the X-ray detector 20 that is spaced from the object 3 by the distance $R_2$. Here, $R_1$ and $R_2$ may be determined according to properties of the object 3 or X-ray imaging conditions.

A space between the object 3 and the X-ray detector 20 is called a free space. While X-rays having passed through the object 3 propagate in the free space, phase shift of X-rays is reflected in the intensity of X-rays detected by the X-ray detector 20. That is, if the object 3 is spaced from the X-ray detector 20 by a given distance such that a free space is present therebetween, data regarding phase shift of X-rays that occurs as X-rays pass through the object 3 is reflected in the intensity of detectable X-rays.

Data regarding various different phase shifts may be needed to acquire a phase contrast image via in-line phase contrast imaging. FIG. 5B illustrates wavefronts 12, 14, and 16 having different distortion degrees depending on propagation distances R2', R2", R2'" of X-rays in the free space. This means that phase shift is reflected, by different degrees, in the intensity of X-rays. That is, different phase shifts are reflected in the intensity of X-rays according to the distance between the object 3 and the X-ray detector 20. Accordingly, as exemplarily shown in FIG. 5B, X-ray detection may be implemented while changing a position of the X-ray detector 20 two or more times to acquire a plurality of different phase contrast image signals, and a phase contrast image is formed using the phase contrast image signals.

However, in the case of forming an image while changing a position of the X-ray detector 20, motion artifacts may occur due to movement of the object 3, and the object 3 may be excessively exposed to radiation because X-ray imaging is implemented plural times.

Accordingly, the X-ray imaging apparatus according to an aspect of an exemplary embodiment is devised to acquire an image signal on a per energy band basis by implementing X-ray imaging at a single position rather than moving the X-ray detector.

Figure 6:
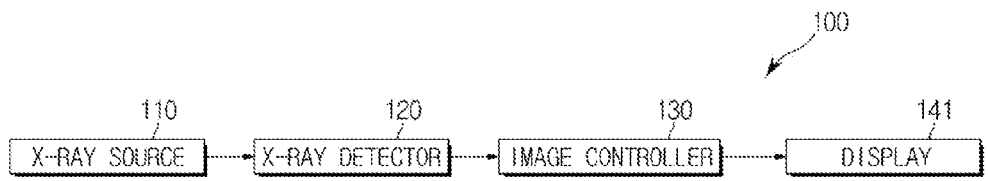
FIG. 6 is a block diagram showing an X-ray imaging apparatus according to an exemplary embodiment.
Figure 7:
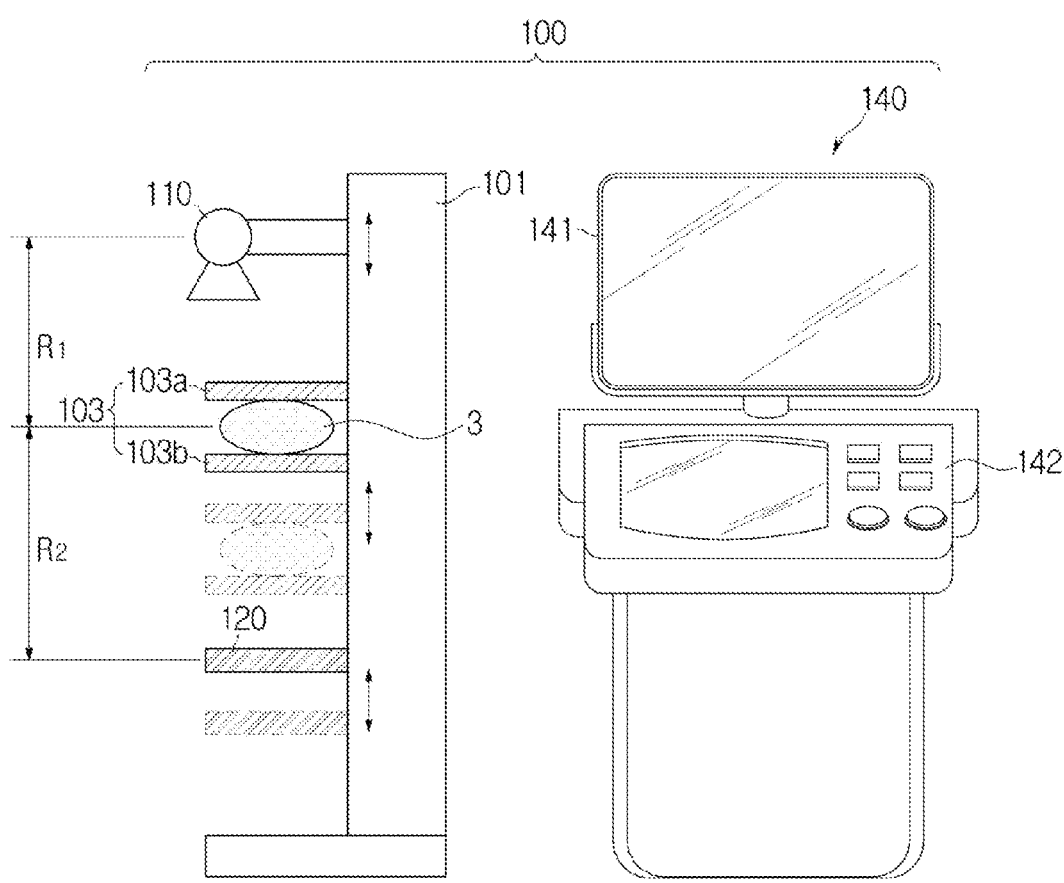
FIG. 7 is a view showing an external appearance of the X-ray imaging apparatus according to an exemplary embodiment.

FIG. 6 is a block diagram showing an X-ray imaging apparatus according to an exemplary embodiment, and FIG. 7 is a view showing an external appearance of the X-ray imaging apparatus according to an exemplary embodiment.

Referring to FIG. 6, the X-ray imaging apparatus 100 includes an X-ray source 110 that generates X-rays to emit X-rays to an object, an X-ray detector 120 that detects X-rays having passed through the object to acquire image signals with respect to a plurality of energy bands, an image controller 130 that acquires quantitative data regarding constituent substances of the object using the image signals on a per energy band basis, and a display 141 that displays the acquired quantitative data. In the following description of the exemplary embodiments, a signal with regard to the intensity of X-rays output from the X-ray detector 120 is referred to as a phase contrast image signal because a phase contrast image may be formed using a signal on a per pixel basis output from the X-ray detector 120.

Referring to FIG. 7, the X-ray source 110 and the X-ray detector 120 may be vertically movably mounted to a housing 101. The object 3 may be fixed by a fixing assembly 103. The fixing assembly 103 may be vertically movably mounted to the housing 101, and may include a support plate 103b to support the object 3 and a compression plate 103a to compress the object 3.

Some objects might not need compression or fixing thereof during X-ray imaging. Accordingly, the fixing assembly 103 may be omitted, or may have only the support plate 103b of the fixing assembly 103 may be included, according to an object to be examined.

The object 3 to be imaged by the X-ray imaging apparatus 100 may be a living body including a human body, or may be any object so long as the transmission of X-rays can be used to derive an internal image thereof.

A distance $R_1$ between the X-ray source 110 and the object 3 may be controlled by adjusting positions of the X-ray source 110 and the fixing assembly 103, and a distance $R_2$ between the object 3 and the X-ray detector 120 may be controlled by adjusting positions of the fixing assembly 103 and the X-ray detector 120.

Once the distance $R_1$ between the X-ray source 110 and the object 3 and the distance $R_2$ between the object 3 and the X-ray detector 120 are appropriately set, the X-ray source 110, the fixing assembly 103, and the X-ray detector 120 are fixed at positions corresponding to the set distances $R_1$ and $R_2$, and then X-ray imaging is implemented.

If the X-ray detector 120 acquires and outputs a plurality of different phase contrast image signals via X-ray imaging, the image controller 130 acquires quantitative data regarding constituent substances of the object using the phase contrast image signals, and forms a phase contrast image or an absorptive image of the object. Here, difference between the phase contrast image signals is not caused by a distance between the object and the X-ray detector 120, but is caused by an energy band corresponding to the phase contrast image signal.

A host device 140 includes the display 141 that displays the image formed by the image controller 130, and an input unit 142 that receives a user instruction with regard to operation of the X-ray imaging apparatus 100.

Hereinafter, operations of the respective components of the X-ray imaging apparatus 100 will be described in detail.

The X-ray source 110 generates X-rays upon receiving electric power from a power supply unit. The energy level of X-rays may be controlled by tube voltage, and X-ray intensity or dose may be controlled by tube current and X-ray exposure time.

If X-rays to be emitted have a predetermined energy band, the energy band may be defined by an upper limit and a lower limit. The upper limit of the energy band, i.e., the maximum energy level of X-rays to be emitted may be adjusted based on the magnitude of tube voltage, and the lower limit of the energy band, i.e., the minimum energy level of X-rays to be emitted may be adjusted by a filter provided inside or outside of the X-ray source 110. Filtering a low energy band of X-rays using the filter may increase an average energy level of X-rays to be emitted.

To form a phase contrast image, all of the X-rays may need to have the same phase. X-rays having the same phase are referred to as spatially coherent X-rays. Accordingly, the X-ray source 110 may be embodied as a device that generates synchrotron radiation, X-ray laser, or high-order harmonics that have great spatial coherence, or may be embodied as a point source, a focal spot of which is reduced using a general X-ray tube.

Figure 8:
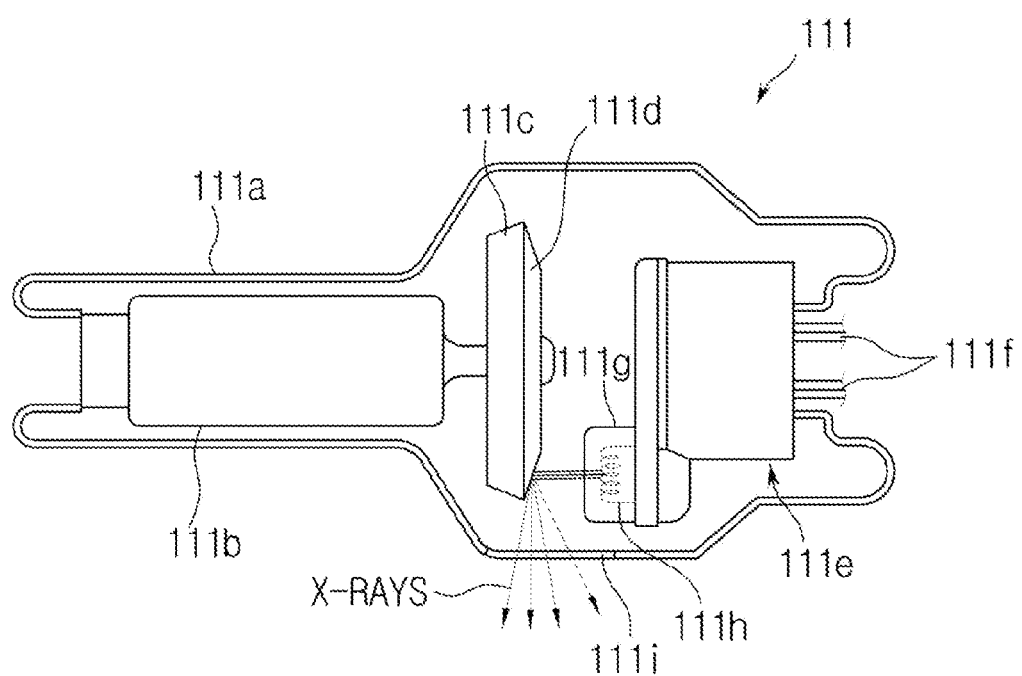
FIG. 8 is a view showing an internal configuration of an X-ray tube included in an X-ray source.

FIG. 8 is a view showing an internal configuration of an X-ray tube included in the X-ray source.

As described above, in an exemplary embodiment, the X-ray imaging apparatus 100 may emit spatially coherent X-rays using an X-ray tube 111.

Referring to FIG. 8, the X-ray tube 111 may be embodied as a diode vacuum tube including an anode 111c and a cathode 111e. The cathode 111e includes a filament 111h and a focusing electrode 111g for focusing of electrons. The focusing electrode 111g is also called a focusing cup.

The interior of a glass tube 111a is evacuated to a pressure of about 10 mmHg, and the filament 111h of the cathode 111e is heated to a high temperature to generate thermal electrons.

As an example, the filament 111h may be a tungsten filament, and may be heated as current is applied to an electrically conductive wire 111f connected to the filament 111b.

The anode 111c may be formed of copper. A target material 111d may be applied to or disposed at one side of the anode 111c facing the cathode 111e. The target material 111d may be a high resistance material, such as Cr, Fe, Co, Ni, W, Mo, etc. As the melting point of the target material 111d increases, the size of the focal spot decreases. Here, the focal spot refers to an effective focal spot. In addition, the target material 111d is tapered by a predetermined angle. As the tapering angle decreases, the size of the focal spot decreases.

If high voltage is applied between the cathode 111e and the anode 111c, thermal electrons are accelerated and collide with the target material 111d of the anode 111c, whereby X-rays are generated. The generated X-rays are emitted outward through a window 111i. The window 111i may be formed of a thin beryllium (Be) film. For example, the filter may be located at the front side or the rear side of the window 111i to filter X-rays having a specific energy band.

The target material 111d may be rotated by a rotor 111b. If the target material 111d is rotated, a heat accumulation rate may be increased by ten times or more on a per unit area basis and the size of the focal spot may be reduced as compared to the case in which the target material 111d is stationary.

Voltage applied between the anode 111c and the cathode 111e of the X-ray tube 111 is referred to as tube voltage, and the magnitude of the tube voltage may be represented as a peak value (kVp). If tube voltage increases, the velocity of thermal electrons increases, and consequently the energy level of X-rays (the energy level of photons) generated via collision between the thermal electrons and the target material increases. Current applied to the X-ray tube 111 is referred to as tube current, and the magnitude of the tube current may be represented as an average value (mA). If the tube current increases, the number of thermal electrons discharged from the filament increases, and consequently X-ray dose (the number of X-ray photons) generated via collision between the thermal electrons and the target material 111d increases.

Accordingly, the energy level of X-rays may be controlled based on tube voltage, and X-ray intensity or dose may be controlled based on tube current and X-ray exposure time. More specifically, if X-rays to be emitted have a predetermined energy band, the energy band may be defined by an upper limit and a lower limit. The upper limit of the energy band, i.e., the maximum energy level of X-rays to be emitted may be adjusted based on the magnitude of tube voltage, and the lower limit of the energy band, i.e. the minimum energy level of X-rays to be emitted may be adjusted by the filter. Filtering a low energy band of X-rays using the filter may increase an average energy level of X-rays to be emitted.

To acquire phase contrast image signals with respect to a plurality of energy bands via the X-ray detector 120, the X-ray source 110 may emit polychromatic X-rays, and an energy band of the polychromatic X-rays may be defined by an upper limit and a lower limit.

In an exemplary embodiment, the X-ray imaging apparatus 100 may emit spatially coherent X-rays using the general X-ray tube 111. For example, if the size of the focal spot is reduced to a range of several micrometers to dozens of micrometers, spatially coherent X-rays may be generated. Although the size of the focal spot is reduced as the melting point and rotation rate of the target material 111d increase and the tapering angle of the target material 111d decreases as described above, the size of the focal spot may vary according to tube voltage, tube current, the size of the filament, the size of the focusing electrode, the distance between the anode and the cathode, etc. Accordingly, reducing the size of the focal spot to a range of several micrometers to dozens of micrometers by adjusting controllable ones of the aforementioned conditions may result in generation of spatially coherent X-rays. In addition, the size of the focal spot may vary according to properties of an object.

Although not shown in the drawings, the X-ray imaging apparatus 100 may include an auto-exposure controller to control imaging conditions, such as tube voltage, tube current, exposure time, the kind of the target material of the anode, the kind of the filter, etc. For example, a pre-shot may be implemented to enable detection of properties of an object from a pre-shot image, which enables imaging conditions suitable for properties of the object to be set. In addition, the distance between the X-ray source 110 and the object 3 and the distance between the object 3 and the X-ray detector 120 may be adjusted according to properties of the object, and the size of the focal spot may be adjusted according to properties of the object.

The X-ray detector 120 detects X-rays having passed through the object, and converts the detected X-rays into electrical signals to acquire phase contrast image signals.

For example, X-ray detectors may be classified based on material composition, conversion of the detected X-rays into electrical signals, and image signal acquisition.

According to the material composition, X-ray detectors may be classified into a single device mode and a hybrid device mode.

In the case of the single device mode, a part that detects X-rays to generate electrical signals and a part that reads out and processes electrical signals may be formed of a single semiconductor material, or may be fabricated via a single process. For example, a single light receiving device, such as a Charge Coupled Device (CCD) or a Complementary Metal Oxide Semiconductor (CMOS), may be used.

In the case of the hybrid device mode, a part that detects X-rays to generate electrical signals and a part that reads out and processes electrical signals may be formed of different materials, or may be fabricated via different processes. For example, the hybrid device mode may include the case in which X-rays are detected by a light receiving device, such as a photodiode or CdZnTe and electrical signals are read out and processed by a CMOS Read Out Integrated Circuit (ROIC), the case in which X-rays are detected by a strip detector and electrical signals are read out and processed by a CMOS ROIC, and the case of using an a-Si or a-Se flat panel system.

In addition, X-ray detectors may be classified into a direct conversion mode and an indirect conversion mode according to conversion of the X-rays into electrical signals.

In the case of the direct conversion mode, electron-hole pairs are temporarily generated in a light receiving device if X-rays are emitted, and by an electric field created around both ends of the light receiving device, electrons move to an anode and holes move to a cathode. An X-ray detector converts this movement into electrical signals. In the direct conversion mode, the light receiving device is formed of a-Se, CdZnTe, $HgI_2$, $PbI_2$, etc.

In the case of the indirect conversion mode, a scintillator is provided between a light receiving device and an X-ray source, and if photons having a visible light wavelength are discharged via reaction between X-rays emitted from the X-ray source and the scintillator, the light receiving device senses the photons and converts the same into electrical signals. In the indirect conversion mode, the light receiving device is formed of a-Si, etc., and the scintillator is a thin-film shaped gadolinium oxysulfide (GADOX) scintillator, a micro-column shaped or needle shaped cesium iodide (CSI (T1)), etc.

In addition, X-ray detectors are classified, according to acquisition of image signals, into a charge integration mode in which a signal is acquired from charges after the charges are stored for a predetermined time and a photon counting mode in which photons having a threshold energy level or more are counted whenever a signal is generated by a single X-ray photon.

Although there is no limit as to material composition and electrical signal conversion of the X-ray detector 120, for convenience of description, an exemplary embodiment using the direct conversion mode in which electrical signals are directly acquired from X-rays and a hybrid mode in which a light receiving device for detection of X-rays and a readout circuit chip are coupled to each other will be described in detail.

Figure 9:
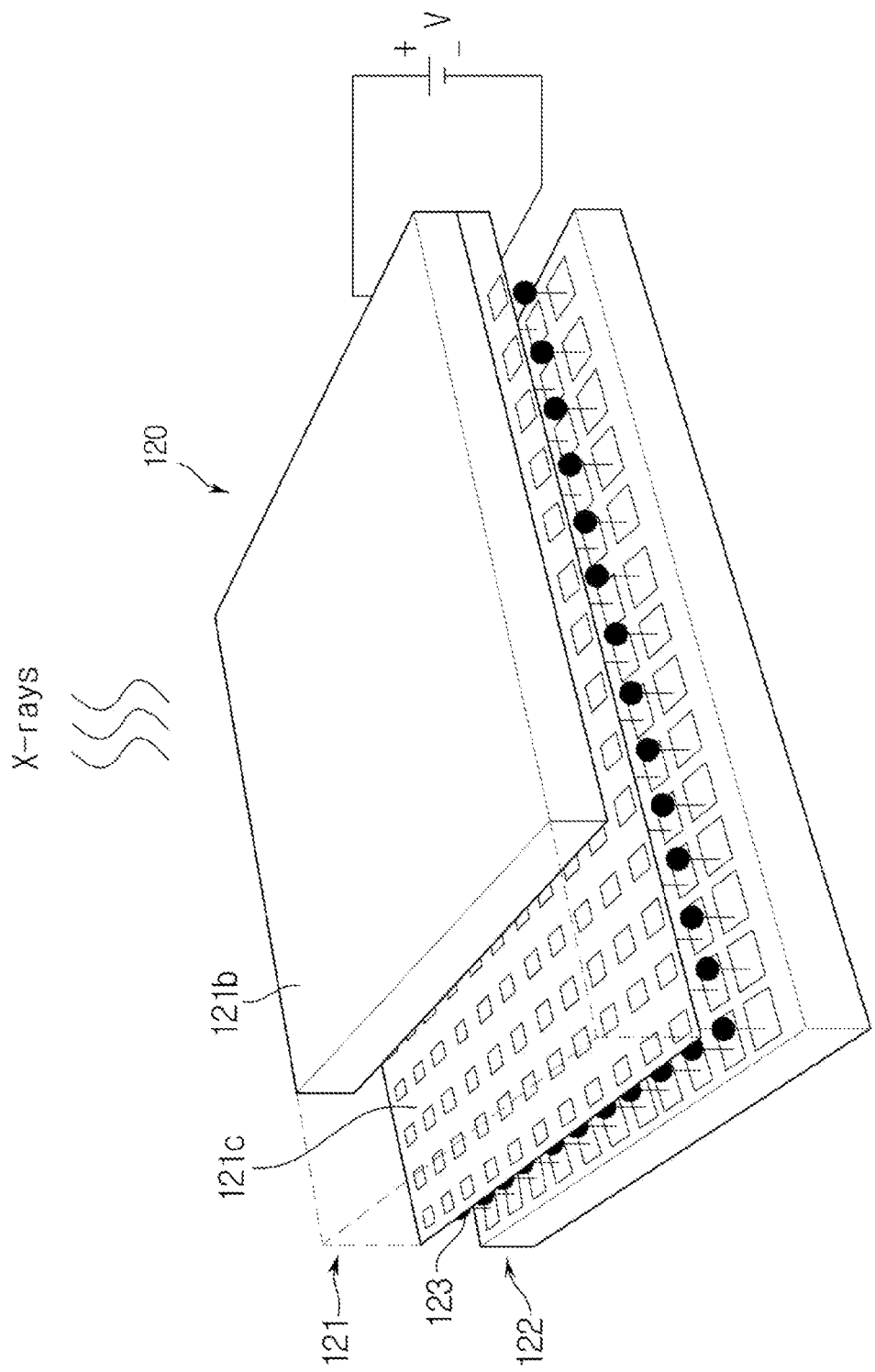
FIG. 9 is a view schematically showing a configuration of an X-ray detector included in the X-ray imaging apparatus according to an exemplary embodiment.

FIG. 9 is a view schematically showing a configuration of the X-ray detector included in the X-ray imaging apparatus according to an exemplary embodiment.

Referring to FIG. 9, the X-ray detector 120 includes a light receiving device 121 that detects X-rays to convert the same into electrical signals, and a readout circuit 122 that reads out the electrical signals. The readout circuit 122 may be formed as a two-dimensional (2D) pixel array including a plurality of pixels. The light receiving device 121 may be formed of a monocrystalline semiconductor material to achieve high dynamic level, high resolution and fast response at a low energy level and a low dose. Examples of the monocrystalline semiconductor material may include Ge, CdTe, CdZnTe, and GaAs.

The light receiving device 121 may be formed as a PIN photodiode in which a p-type layer 121c in which p-type semiconductors are arranged in a 2D pixel array is bonded to the bottom surface of a high-resistance n-type semiconductor substrate 121b. The readout circuit 122 is formed of a CMOS and is coupled to the light receiving device 121 on a per pixel basis. The CMOS readout circuit 122 and the light receiving device 121 may be bonded to each other via flip-chip bonding as bumps 123 formed of PbSn, In, etc. are reflow soldered and thermally pressed. The above-described configuration is an example of the X-ray detector 120, and the configuration of the X-ray detector 120 is not limited thereto.

The X-ray imaging apparatus 100 acquires phase contrast image signals with respect to a plurality of different energy bands to generate a phase contrast image of an object. For example, the X-ray source 110 may emit X-rays having different energy bands respectively, or the X-ray source 110 may emit wideband X-rays including a plurality of energy bands once and the X-ray detector 120 may separate the detected X-rays into a plurality of energy bands.

Figure 10:
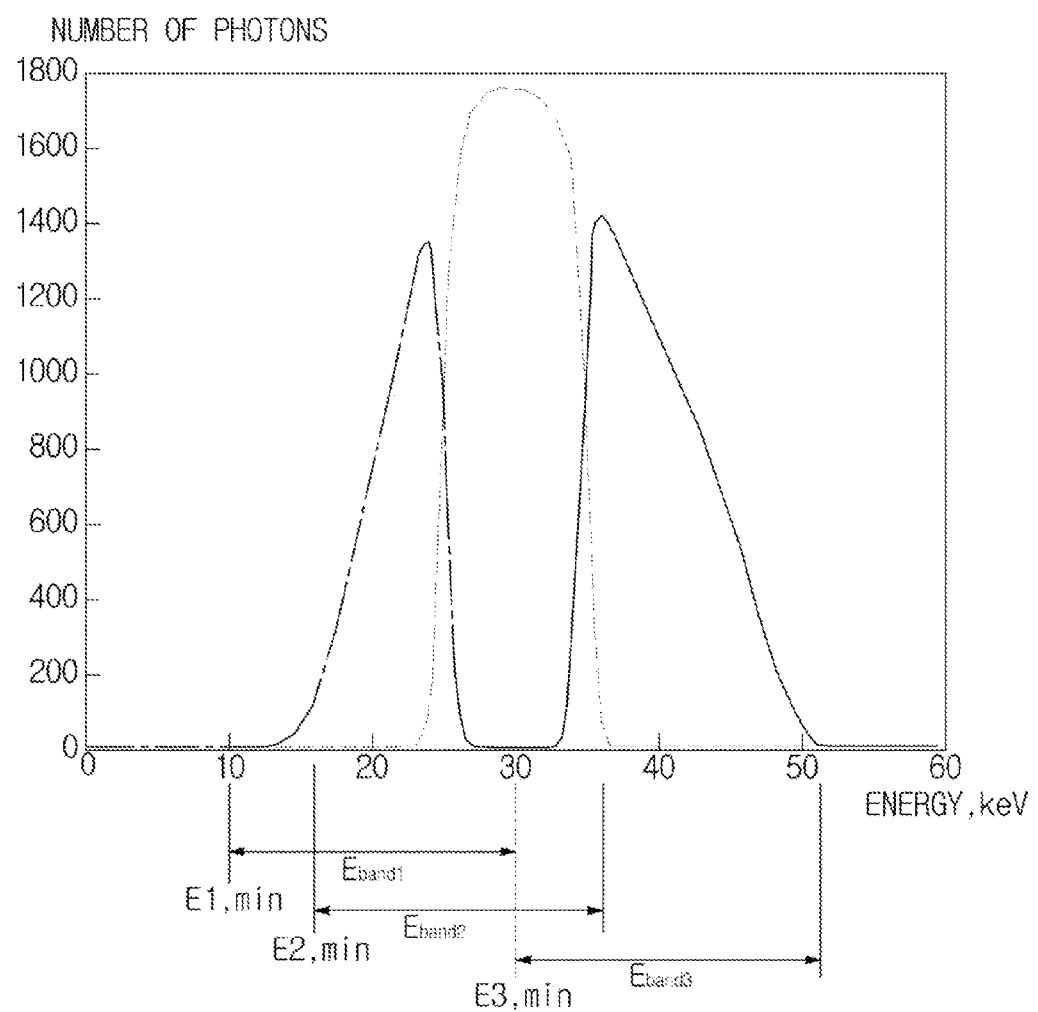
FIG. 10 is a graph schematically showing energy bands of X-rays that may be emitted from the X-ray source.

FIG. 10 is a graph schematically showing energy bands of X-rays that may be emitted from the X-ray source.

To acquire phase contrast image signals with respect to different energy bands, the X-ray source 110 may emit X-rays having different energy bands, respectively. An example of energy bands of X-rays to be emitted is shown in FIG. 10.

Referring to FIG. 10, the X-ray source 110 may respectively emit X-rays having a first energy band E1, X-rays having a second energy band E2, and X-rays having a third energy band E3. The plurality of energy bands may partially overlap each other.

For example, to emit the X-rays having the first energy band E1, a tube voltage of 25 kVp is supplied to the X-ray source 110 to generate X-rays having the maximum energy $E1_{max}$ of 25 keV. Then, the minimum energy $E1_{min}$ of X-rays to be emitted is adjusted to 10 keV using the filter provided inside or outside of the X-ray source 110. Thereby, emission of X-rays having the first energy band (E1: 10~25 keV) is accomplished.

To emit X-rays having the second energy band E2, a tube voltage of 35 kVp is supplied to the X-ray source 110 to generate X-rays having the maximum energy $E2_{max}$ of 35 keV. Then, the minimum energy $E2_{min}$ of X-rays to be emitted is adjusted to 15 keV using the filter provided inside or outside of the X-ray source 110. Thereby, emission of X-rays having the second energy band (E2: 15~35 keV) is accomplished.

To emit X-rays having the third energy band E3, a tube voltage of 50 kVp is supplied to the X-ray source 110 to generate X-rays having the maximum energy $E3_{max}$ of 50 keV. Then, the minimum energy $E3_{min}$ of X-rays to be emitted is adjusted to 30 keV using the filter provided inside or outside of the X-ray source 110. Thereby, emission of X-rays having the third energy band (E3: 30~50 keV) is accomplished.

The X-ray detector 120 detects X-rays having different energy bands respectively, and converts the detected X-rays into electrical signals, i.e., phase contrast image signals to transmit the same to the image controller 130.

In another exemplary embodiment to acquire phase contrast image signals with respect to different energy bands, as described above, the X-ray detector 120 may detect X-rays and separate the detected X-rays into a plurality of energy bands.

For example, the X-ray source 110 emits wideband X-rays including a plurality of energy bands E1 to E3, and the X-ray detector 120 detects X-rays having passed through the object to separate the detected X-rays into the plurality of energy bands E1, E2 and E3. Hereinafter, a configuration of the X-ray detector 120, which may serve to divide the detected X-rays into a plurality of energy bands, will be described.

Figure 11A:
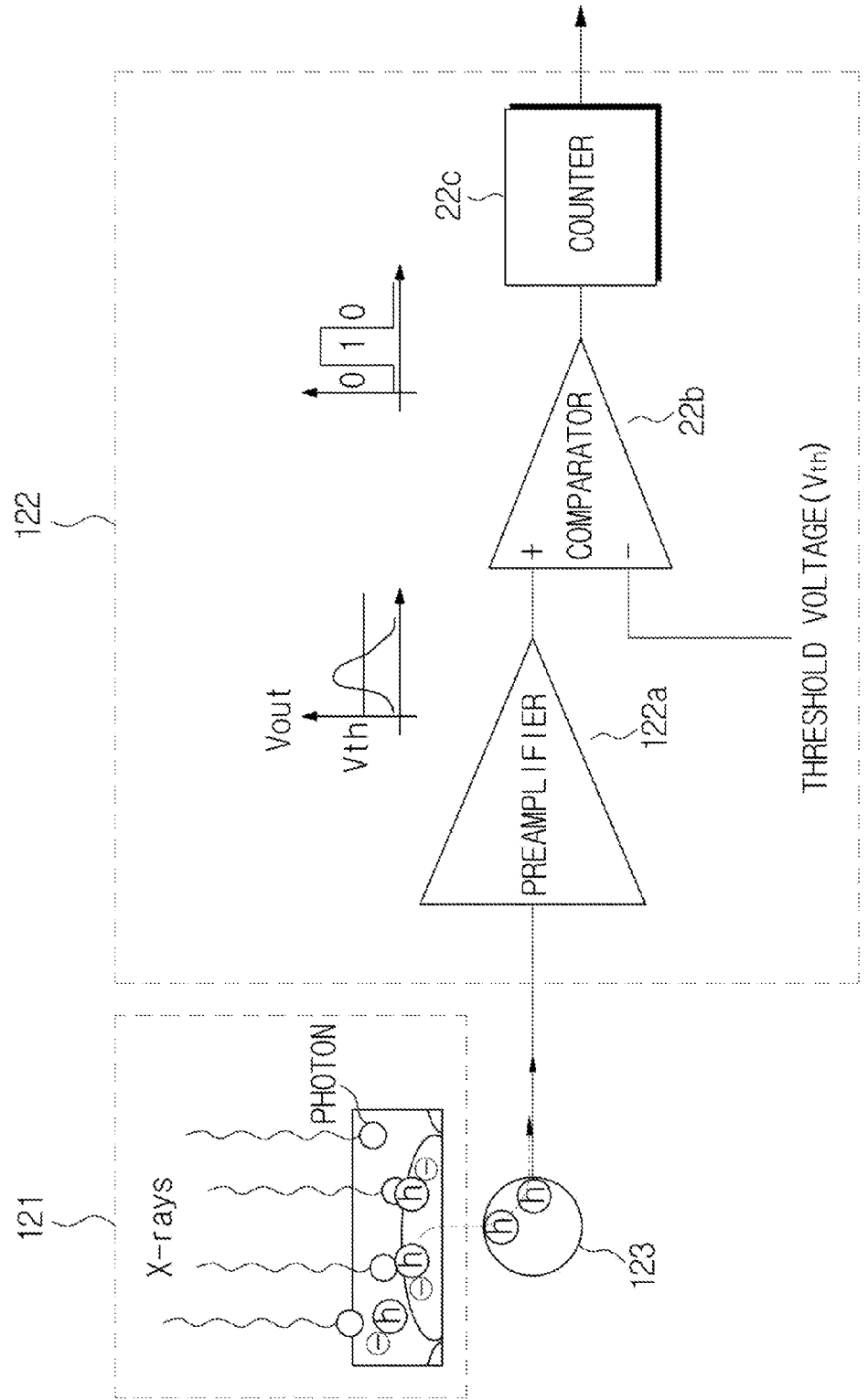
FIG. 11A is a view schematically showing a configuration of a single pixel.
Figure 11B:
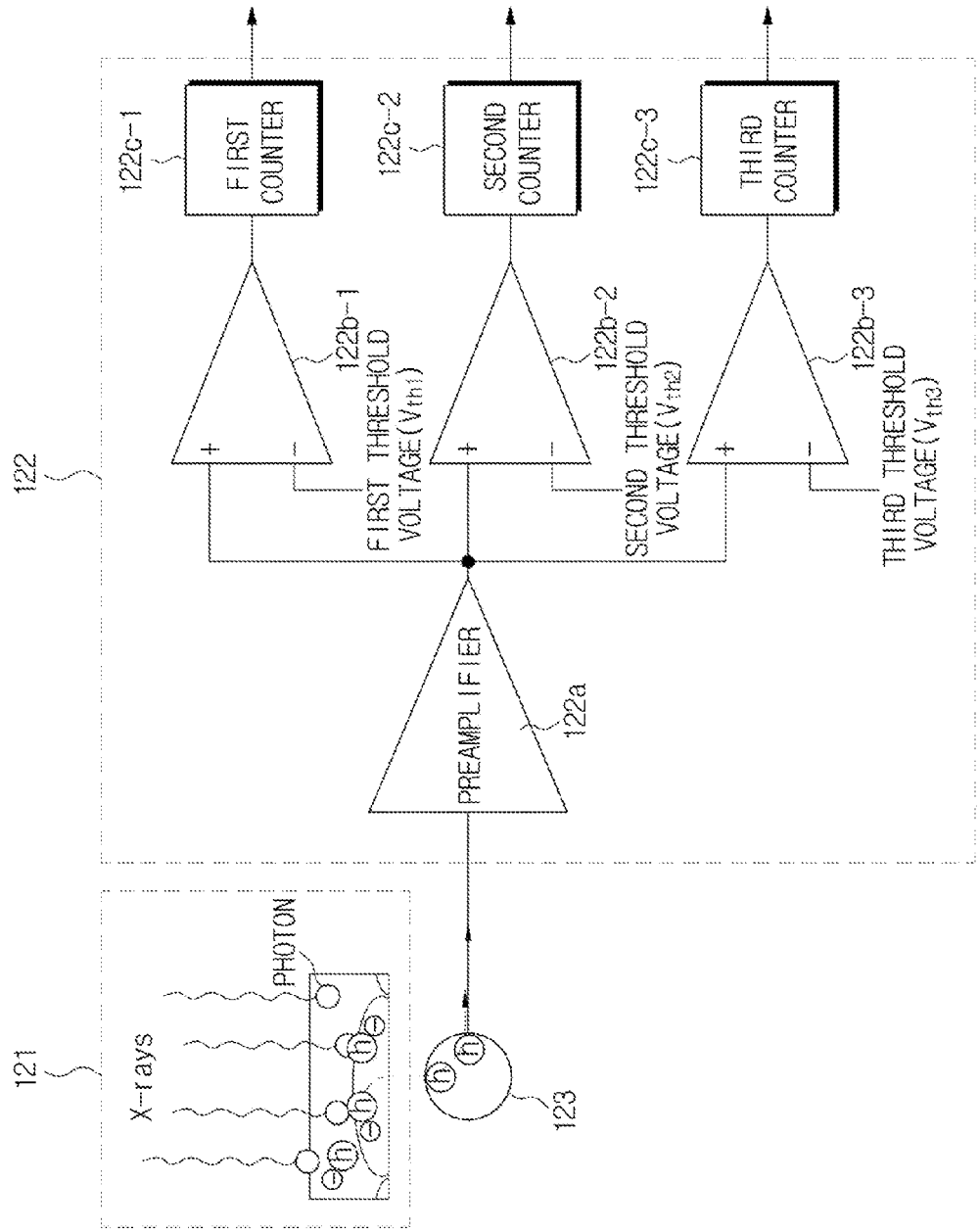
FIG. 11B is a view schematically showing a configuration which may separate detected X-rays into a plurality of energy bands.

FIG. 11A is a view schematically showing a configuration of a single pixel of the X-ray detector shown in FIG. 9, and FIG. 11B is a view schematically showing a configuration of a single pixel which may separate detected X-rays into a plurality of energy bands.

Referring to FIG. 11A, if photons of X-rays are introduced into the light receiving device 121, electrons of a valence band receive energy of photons and are excited to a conduction band beyond a band gap energy difference. This results in generation of electron-hole pairs in a depletion region.

If metal electrodes are provided respectively at a p-type layer and an n-type substrate of the light receiving device 121 and reverse bias is applied to the metal electrodes, electrons among the electron-hole pairs generated in the depletion region are dragged to an n-type region and holes are dragged to a p-type region. Then, as the holes dragged to the p-type region are input to the readout circuit 122 through the bonding bumps 123, readout of electrical signals generated by the photons may be possible. However, the electrons may be input to the readout circuit 122 to generate electrical signals according to a configuration of the light receiving device 121 and the applied voltage, for example.

The readout circuit 122 may take the form of a 2D pixel array of the light receiving device 121 corresponding to p-type semiconductors. Thus, the readout circuit 122 reads out electrical signals on a per pixel basis. If charges of the light receiving device 121 are input to the readout circuit 122 through the bonding bumps 123, a preamplifier 122a of the readout circuit 122 accumulates the input charges generated per photon, and outputs a corresponding voltage signal.

The voltage signal output from the preamplifier 122a is transmitted to a comparator 22b. A comparator 22b compares the input voltage signal with a threshold voltage that may be controlled from the outside, and outputs a pulse signal of '0' or '1' based on the comparison result. A counter 22c outputs a digital image signal by counting how many times the pulse signal of '1' appears. An X-ray image of the object may be acquired via combination of image signals on a per pixel basis.

Here, the threshold voltage corresponds to threshold energy. To count the number of photons having threshold energy E or more, threshold voltage corresponding to the threshold energy E is input to the comparator 22b. The correspondence between threshold energy and threshold voltage is based on the fact that the magnitude of an electrical signal (voltage) generated from the light receiving device is variable according to energy of photons. Thus, threshold voltage corresponding to desired threshold energy may be calculated using a relational expression between voltage and energy of photons. In the following description of the exemplary embodiments, inputting threshold energy to the X-ray detector 120 may refer to inputting threshold voltage corresponding to the threshold energy.

In the X-ray imaging apparatus 100 according to an exemplary embodiment, to acquire different phase contrast image signals on a per energy band basis, the X-ray source 110 may emit X-rays having a plurality of energy bands, i.e., wideband X-rays once, and the X-ray detector 120 may detect the X-rays to separate the same into a plurality of energy bands.

As exemplarily shown in FIG. 11B, a plurality of comparators and a plurality of counters may be provided to count photons separated into a plurality of energy bands. Although the exemplary configuration of FIG. 11B includes three comparators and three counters, an exemplary embodiment is not limited thereto, and the number of comparators and counters may be determined according to the number of energy bands to be separated.

Referring to FIG. 11B, if electrons or holes generated per photon are input to the preamplifier 122a such that a voltage signal is output, the voltage signal is input to three comparators 122b-1, 122b-2, and 122b-3. Then, if first threshold voltage $V_{th1}$, second threshold voltage $V_{th2}$, and third threshold voltage $V_{th3}$ are input to the respective comparators, the first comparator 122b-1 compares the first threshold voltage with input voltage, and a first counter 122c-1 counts the number of photons that generate voltage greater than the first threshold voltage. In the same manner, the second comparator 122b-2 compares the second threshold voltage with input voltage, and a second counter 122c-2 counts the number of photons that generate voltage greater than the second threshold voltage. The third comparator 122b-3 compares the third threshold voltage with input voltage, and a third counter 122c-3 counts the number of photons that generate voltage greater than the third threshold voltage.

The energy spectrum exemplarily shown in FIG. 10 and the configuration of the X-ray detector exemplarily shown in FIGS. 11A and 11B are given only as an example, and the energy bands of X-rays to be emitted and separated by the X-ray imaging apparatus 100 and the corresponding configuration of the X-ray detector are not limited to the exemplary illustration. As described above, the energy bands of X-rays to be generated and emitted by the X-ray source 110 may vary according to properties of the object, and the range and number of the energy bands separated by the X-ray detector 120 may vary according to properties of the object or the definition or resolution of a desired phase contrast image. The greater the number of energy bands to be separated, the greater the edge enhancement as well as the greater the definition of the phase contrast image.

As the X-ray source 110 emits different energy bands of X-rays respectively, or the X-ray detector 120 separates detected X-rays on a per energy band basis, the X-ray detector 120 may acquire and output phase contrast image signals on a per energy band basis.

The image controller 130 may acquire quantitative data regarding constituent substances of an object using phase contrast image signals on a per energy band basis, and generate a phase contrast image or absorptive image of the object to output the same via the display 141.

Figure 12:
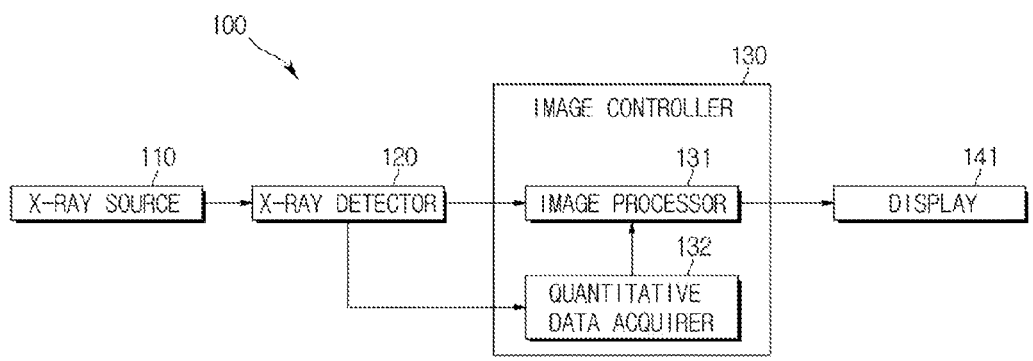
FIG. 12 is a control block diagram of the X-ray imaging apparatus according to an exemplary embodiment.
Figure 13:
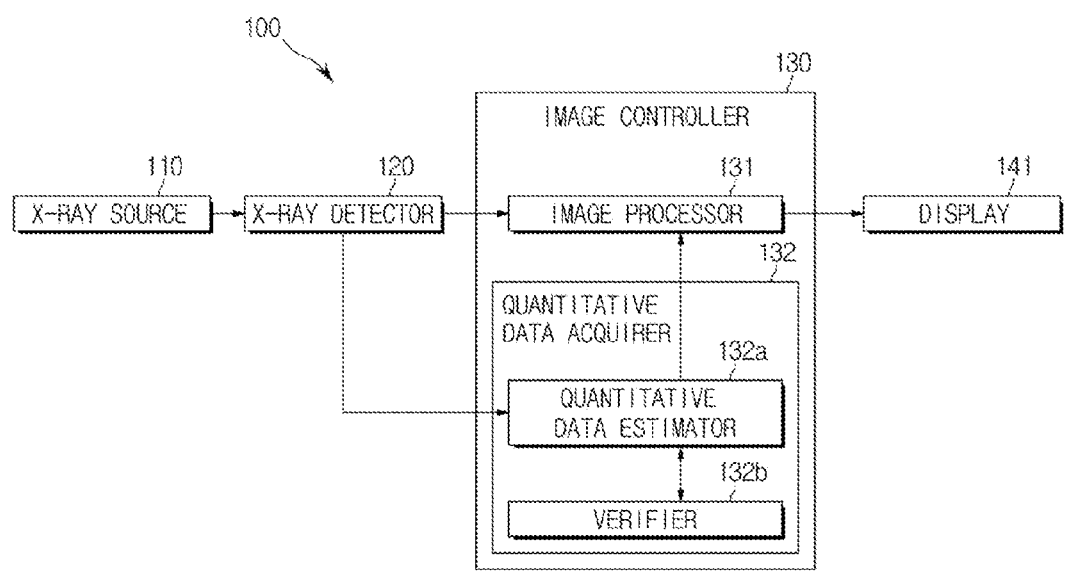
FIG. 13 is a control block diagram showing a configuration of a quantitative data acquirer.

FIG. 12 is a control block diagram of an X-ray imaging apparatus according to an exemplary embodiment, and FIG. 13 is a control block diagram showing a configuration of a quantitative data acquirer included in the image controller.

Referring to FIG. 12, the image controller 130 of the X-ray imaging apparatus 100 includes an image processor 131 that generates a phase contrast image of an object using phase contrast image signals on per energy band basis output from the X-ray detector 120, and a quantitative data acquirer 132 that acquires quantitative data regarding constituent substances of the object using the phase contrast image signals.

Referring to FIG. 13, the quantitative data acquirer 132 may include a quantitative data estimator 132a that estimates quantitative data regarding constituent substances of the object, and a verifier 132b that verifies the estimated quantitative data. Hereinafter, an exemplary embodiment of the quantitative data acquirer 132 will be described in detail.

Constituent substances of the object are substances composing the interior of the object. For example, if the object is a living body, constituent substances thereof may include bone and soft tissue. More specifically, if the object is the breast of a human body, constituent substances may include fibrous tissues, fibroglandular tissues, and adipose tissues. Since every subject may have different numbers and kinds of internal constituent substances, it is assumed that the object includes at least one constituent substance.

More specifically, the quantitative data estimator 132a may calculate approximate quantitative data using a relational expression between quantitative data and phase contrast image signals on a per different energy band basis, and may estimate quantitative data regarding constituent substances by iteratively applying a regularization function to the approximate quantitative data.

The verifier 132b judges whether the estimated quantitative data satisfies a preset verification requirement, i.e., a criteria or criterion, in order to verify reliability of the estimated quantitative data.

An example of the quantitative data that may be acquired by the X-ray imaging apparatus 100 may include the thickness of constituent substances. Hereinafter, an exemplary embodiment in which the quantitative data acquirer 132 acquires the thickness of constituent substances will be described.

A relationship between phase contrast image signals on a per energy band basis and a thickness $t_j$ of M constituent substances (M being an integer ≥1) may be represented by the following Equation 1 using a $\mu_{ji}$ which is an absorption coefficient corresponding to an $i^{th}$ energy band among a plurality of different energy bands and a $\phi_{ji}$ which is a phase shift coefficient corresponding to the $i^{th}$ energy band among a plurality of different energy bands.

$$-\ln(I_{Ei}/I_{Ei}^{FF}) \cong \sum_{j=1}^{M}(\mu_{ji}+\phi_{ji}k^{-1}z\nabla^2)t_j \qquad \text{Equation 1}$$

$I_{Ei}$ denotes a phase contrast image signal corresponding to the $i^{th}$ energy band among a plurality of different energy bands, and $I_{Ei}^{FF}$ denotes a flat-field image signal in the corresponding energy band. Both $I_{Ei}$ and $I_{Ei}^{FF}$ may be pixel values, or may be representative values of a predefined region. Z denotes a distance between the object and the X-ray detector 120, i.e., a free space propagation distance.

Assuming that the total thickness L of the object is known, the above Equation 1 may be represented by the following Equation 2.

$$-\ln(I_{Ei}/I_{Ei}^{FF}) \cong \mu_{1i}L+\sum_{j=2}^{M}[\Delta\mu_{j1}+\Delta\phi_{j1}k^{-1}z\nabla^2]t_i \qquad \text{Equation 2}$$

Here, $\Delta\mu_{ji} \equiv \mu_{ji}-\mu_{ji}$ and $\Delta\phi_{ji} \equiv \phi_{ji}-\phi_{ji}$. If the X-ray detector 120 acquires phase contrast image signals corresponding to N different energy bands (N being an integer $\geq M$), the quantitative data estimator 132a may calculate respective approximate thicknesses of the M constituent substances using Equation 2. For example, the absorption coefficient $\mu_{ji}$ and the phase shift coefficient $\phi_{ji}$ of each substance may be preset as pre-data by the quantitative data estimator 132a, and the total thickness L of the object may be set based on data given by the fixing assembly 103 regarding a distance between the compression plate 103a and the support plate 103b. The calculation of the approximate thickness using Equation 2 may be implemented on a per predefined region basis.

The quantitative data estimator 132a may iteratively apply a regularization function to the calculated approximate thickness, in order to improve reliability of the estimated thickness data. In one example, a regularization function as represented by the following Equation 3 may be applied.

$$\tilde{T}(\vec{r}) = \mathrm{argmin}\left[\|AT(\vec{r})-P(\vec{r})\|^2+\sum_{j=2}^{M}\alpha_j\|\nabla t_j(\vec{r})\|^2\right], \text{ where} \qquad \text{Equation 3}$$

$T(\vec{r}) = [t_2(\vec{r}), t_3(\vec{r}), \ldots, t_M(\vec{r})];$ and $P(\vec{r}) = [p_1(\vec{r}), p_2(\vec{r}), \ldots, p_N(\vec{r})].$ A is an operator that converts the thickness of constituent substances into $p_i \equiv -\ln(I_{Ei}/I_{Ei}^{FF})-\mu_{ji}L$ according to Equation 2, and $\alpha_j$ is a specific constant value for adjustment of an error retrieval ratio. $\tilde{T}(\vec{r})$ is thickness data newly estimated by Equation 3. New thickness data is estimated by substituting the estimated thickness data into the ArgMin function of Equation 3.

The regularization function of Equation 3 is a function to minimize an error of estimated thickness data and is an example of the regularization function. Thus, regularization applied by the quantitative data estimator 132a is not limited to Equation 3.

The verifier 132b verifies reliability of the estimated thickness data to judge whether to stop application of the regularization function. For example, the verifier 132b judges whether the estimated thickness data satisfies a verification requirement. One example of the verification requirement may include whether the regularization function is applied predetermined times, or whether a thickness error value is a preset reference value or less. If the verifier 132b judges that the estimated thickness data satisfies the verification requirement, a value finally estimated by the quantitative data estimator 132a becomes thickness data finally acquired by the quantitative data acquirer 132. Conversely, if the verifier 132b judges that the estimated thickness data does not satisfy the verification requirement, the quantitative data estimator 132a again applies the regularization function to estimate a new thickness. Verification by the verifier 132b may be implemented whenever the regularization function is applied, i.e., whenever thickness data is estimated, or may be implemented whenever application of the regularization function is implemented predetermined times.

Quantitative data acquired by the quantitative data acquirer 132 may be supplied to a user in various ways. In one example, the quantitative data may be displayed, or an image containing the quantitative data may be displayed via the display 141. Display of the image containing the quantitative data will be described later.

Figure 14:
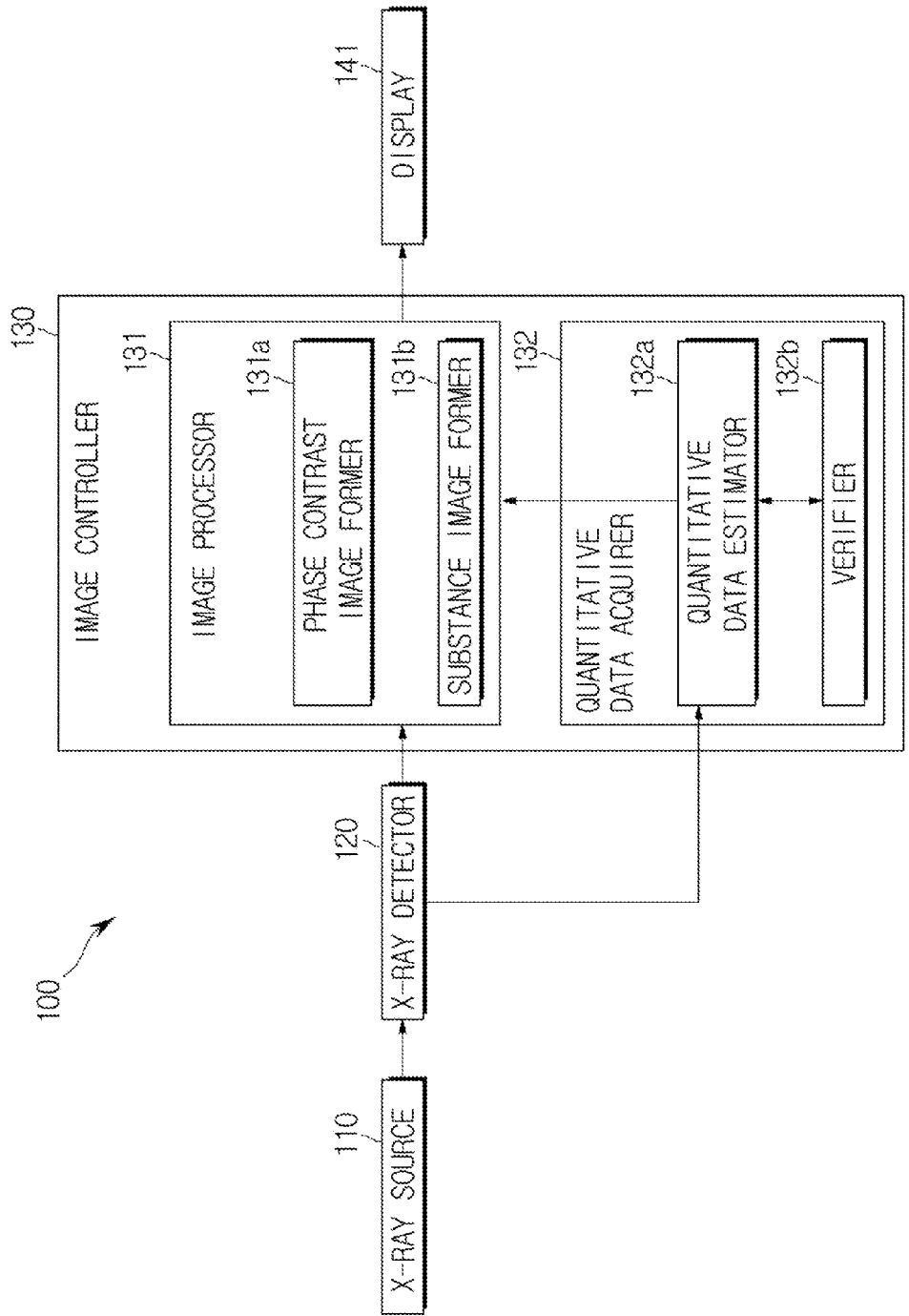
FIG. 14 is a control block diagram showing a configuration of an image processor of the X-ray imaging apparatus according to an exemplary embodiment.

FIG. 14 is a control block diagram showing a configuration of the image processor of the X-ray imaging apparatus according to an exemplary embodiment.

Referring to FIG. 14, the image processor 131 may include a phase contrast image former 131a that forms a phase contrast image of the object, and a substance image former 131b that forms a substance image on a per constituent substance basis.

The phase contrast image former 131a forms a phase contrast image of the object using phase contrast image signals on a per energy band basis output from the X-ray detector 120. Hereinafter, an exemplary embodiment with regard to formation of the phase contrast image will be described in detail.

Figure 15:
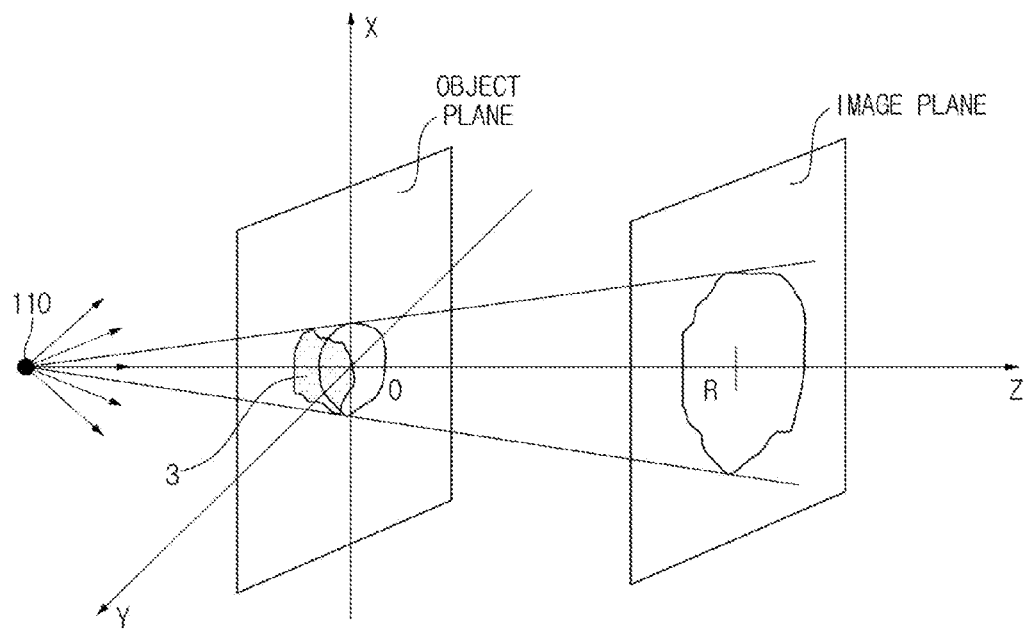
FIG. 15 is a view geometrically showing positions of an object and the X-ray detector.

FIG. 15 is a view geometrically showing positions of the object and the X-ray detector for explanation of phase retrieval.

The phase contrast image former 131a implements phase retrieval from phase contrast image signals output from the X-ray detector 120. For example, the geometrical relationship shown in FIG. 15 may be used. Referring to FIG. 15, it is assumed that the object 3 and the X-ray detector 120 are located in a three-dimensional (3D) space that is defined by x-axis, y-axis and z-axis coordinates, the object 3 is present on an object plane, and the X-ray detector 120 is present on an image plane. Here, it is assumed that the z-axis corresponds to an optical axis along which X-rays propagate, the object plane is defined such that the z-axis passes the zero point (z=0), and the image plane is defined such that the z-axis passes a point R (z=R).

The intensity I and phase distribution $\phi$ of the detected X-rays may be represented in terms of line integrals of the complex index of refraction. The complex index of refraction n may be defined by the following Equation 4.

$$n(r)=1-\delta-i\beta \qquad \text{Equation 4}$$

Here, the imaginary number $\beta$ denotes X-ray absorption or attenuation, the real number $\delta$ denotes phase shift due to constituent substances of the object; n satisfies $|n-1|\ll 1$, and r is defined as $(r\perp, z)$.

The intensity I and phase distribution $\phi$ of X-rays are defined by the following Equation 5 and Equation 6.

$$I(r\perp,0,\lambda)=\exp[-M(r\perp,0,\lambda)], \text{ where}$$

$$M(r\perp,0,\lambda)=(4\pi/\lambda)\int_{-\infty}^{0}\beta(r\perp,z',\lambda)dz' \qquad \text{Equation 5}$$

$$\phi(r\perp,0,\lambda)=-(2\pi/\lambda)\int_{-\infty}^{0}\delta(r\perp,z',\lambda)dz' \qquad \text{Equation 6}$$

where M denotes absorption or attenuation. Wavelength ($\lambda$) dependence of the imaginary number $\beta$ and the real number $\delta$ of the complex index of refraction n may be represented by the following Equation 7 and Equation 8.

$$\beta(\lambda)=(\lambda/\lambda_0)^4\beta(\lambda_0), \quad \text{Equation 7}$$

$$\delta(\lambda)=(\lambda/\lambda_0)^2\delta(\lambda_0) \quad \text{Equation 8}$$

X-ray propagation from the object plane (z=0) to the image plane (z=R) may be represented by Fresnel integral. The Fresnel integral may be approximated by the following Equation 9 using a Transport of Intensity Equation (TIE).

$$(R\lambda/2\pi)[-\nabla^2\phi(r\perp,0,\lambda)-\nabla\phi(r\perp,0,\lambda)\cdot\nabla \ln I(r\perp,0,\lambda)]=I(r\perp,R,\lambda)/I(r\perp,0,\lambda)-1 \quad \text{Equation 9}$$

In Equation 9, if X-ray intensity distribution in the object plane does not greatly differ from X-ray intensity distribution in the image plane, the right side may be replaced with $\ln[I(r\perp,\tilde{R},\lambda)]-\ln[I(r\perp,0,\lambda)]$.

Equation 9 may be represented by the following Equation 10 by synthesizing Equation 5 to Equation 8.

$$-\sigma^3 M(r\perp,0,\lambda_0)+\gamma\sigma(-\nabla^2\phi)(r\perp,0,\lambda_0)+\gamma\sigma^4\nabla\phi(r\perp,0,\lambda_0)\cdot\nabla M(r\perp,0,\lambda_0)=\ln[I(r\perp,R,\lambda)] \quad \text{Equation 10}$$

where $\sigma=\lambda/\lambda_0$ and $\gamma=R\lambda/2\pi$. For example, if the X-ray detector 120 separates phase contrast image signals into three energy bands, i.e., if phase contrast image signals correspond to three different wavelengths $\lambda_0$, $\lambda_1$, and $\lambda_2$, the following Equation 11 may be defined.

$$A\begin{pmatrix} M(r_\perp,0,\lambda_0) \\ -\nabla^2\varphi(r_\perp,0,\lambda_0) \\ \nabla M \cdot \nabla\varphi(r_\perp,0,\lambda_0) \end{pmatrix} = \begin{pmatrix} F_0 \\ F_1 \\ F_2 \end{pmatrix} \quad \text{Equation 11}$$

$$A = \begin{pmatrix} -1 & \gamma_0 & \gamma_0 \\ -\sigma_1^3 & \sigma_1\gamma_1 & \sigma_1^4\gamma_1 \\ -\sigma_2^3 & \sigma_2\gamma_2 & \sigma_2^4\gamma_2 \end{pmatrix}.$$

The function of the right side $F_j=\ln[I(r\perp,R,\lambda_j)]$ may be calculated using phase contrast image signals with respect to three energy bands output from the X-ray detector 120, i.e., the intensity of X-rays with respect to three energy bands. Thus, M representing X-ray attenuation and Laplacian phase distribution may be acquired as the value of Equation 1, and phase distribution may be retrieved by calculating the Poisson equation represented by the following Equation 12.

$$-\nabla^2\phi(r\perp,0,\lambda_0)=\Sigma A_{1j}^{-1}F_j \quad \text{Equation 12}$$

If phase distribution $\phi$ is retrieved, the complex index of refraction n is determined by Equation 4 to Equation 6. The phase contrast image former 131a may determine a value of the complex index of refraction n via the above-described procedure, and form a phase contrast image of the object using the determined value. The formed phase contrast image of the object may clearly show the profile of constituent substances of the object and may vividly show even small details.

The phase contrast image former 131a may implement image calibration for enhancement in the quality of an X-ray image, such as flat field correction, noise reduction, etc. The calibrated phase contrast image of the object may be displayed via the display 141.

The image processor 130 may form an absorptive image not containing X-ray phase contrast data. For example, the image processor 130 may selectively form an absorptive image or a phase contrast image or may form both the absorptive image and the phase contrast image to display the same via the display 141. To form the absorptive image, X-ray imaging may be performed in a state in which the distance $R_2$ between the object 3 and the X-ray detector 120 becomes zero.

The substance image former 131b forms a substance image containing quantitative data regarding constituent substances acquired by the quantitative data acquirer 132. In an exemplary embodiment, if the quantitative data acquirer 132 acquires thickness data on a per constituent substance basis, the substance image former 131b forms a substance image containing the thickness data. The substance image is an image in which at least one constituent substance among constituent substances of the object is displayed along with thickness data thereof. For example, a lesion image shows data regarding the thickness of a lesion among constituent substances of the object. The substance image containing thickness data may be acquired in various ways.

For example, brightness of each pixel corresponding to a constituent substance may correspond to thickness data with respect to the corresponding pixel. The pixel corresponding to the constituent substance refers to a pixel of a region where the corresponding constituent substance of the substance image is located. Based on a relationship between the thickness of the constituent substance and penetration amounts of X-rays, brightness of the pixel may increase as the thickness of the constituent substance increases, and the inverse case is also possible. In addition, thickness data with regard to each pixel may be quantitatively displayed.

One substance image may show only one constituent substance, or may show two or more constituent substances that do not overlap each other in an X-ray transmission direction.

The formed substance image may be displayed via the display 141.

The substance image former 131b may form substance images of all constituent substances of the object, or may form substance images of some constituent substances.

In addition, formation or display of the substance images may be selected by a user. The user may input selection for a constituent substance via the input unit 142 of the host device 140. For example, if a phase contrast image or an absorptive image of the object is displayed via the display 141 and the user inputs selection for a specific constituent substance based on the displayed image, the substance image former 131b may form a substance image of the selected constituent substance. Alternatively, the substance image former 131b may form and store a substance image of all constituent substances, and may display only a substance image for constituent substances selected by the user.

Alternatively, to enable thickness data regarding each constituent substance of the object to be checked from a single image, different color channels may be mapped to the respective substance images formed by the substance image former 131b, and the resulting images may be composed to output a single image. For example, in the case of using an RGB color space, an R channel may be mapped to a constituent substance A, a G channel may be mapped to a constituent substance B, and a B channel may be mapped to a constituent substance C. There is no limit as to the color space used in the exemplary embodiments. For example, various other color spaces, such as a YCbCr color space, a CMY color space, a CMYK color space, etc., may be used.

Thickness data contained in each substance image is represented as a mapped channel value. For example, in the image of the constituent substance A, a value of the R channel of each pixel may vary according to thickness data on a per pixel basis. This is equally applied to the other two images.

In the composite image displayed on the display 141, the respective constituent substances are distinguished by different colors, and thickness data regarding the respective constituent substances may be represented as brightness.

Figure 16:
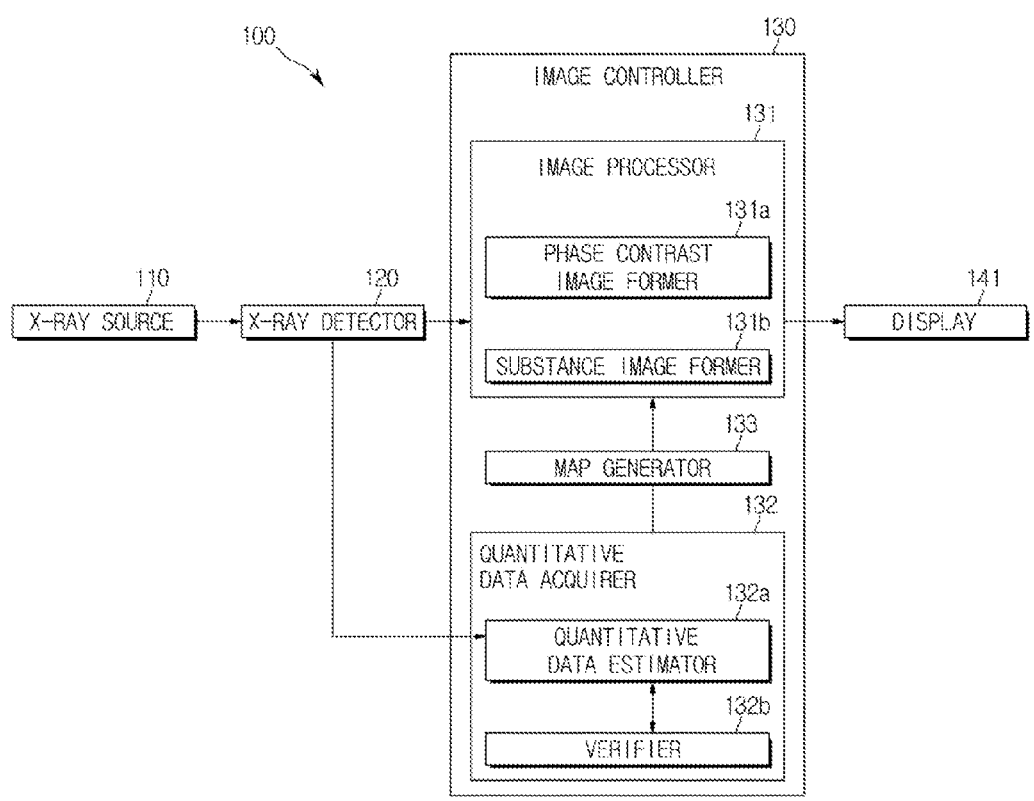
FIG. 16 is a control block diagram of the X-ray imaging apparatus that may generate a quantitative data map.

FIG. 16 is a control block diagram of the X-ray imaging apparatus that may generate a quantitative data map.

Referring to FIG. 16, the image controller 130 may further include a map generator 133 that generates a quantitative data map on a per constituent substance basis. In the quantitative data map, quantitative data acquired by the quantitative data acquirer 132 is mapped on a per pixel basis or on a per preset region basis.

Assuming that the acquired quantitative data is thickness data, the map generator 133 generates a thickness data map by mapping the thickness data acquired by the quantitative data acquirer 132 to a corresponding pixel or a preset region. For example, if the constituent substance A is located over m pixels, thickness data regarding the constituent substance A corresponding to each of the m pixels may be mapped on a per pixel basis and stored in a thickness data map of the constituent substance A. The map generator 133 generates and stores the thickness data map on a per constituent substance basis.

The image processor 131 may provide the user with quantitative data on a per constituent substance basis using the quantitative data map stored in the map generator 133.

Hereinafter, an exemplary embodiment with regard to a control method for the X-ray imaging apparatus according to an exemplary embodiment will be described.

Figure 17:
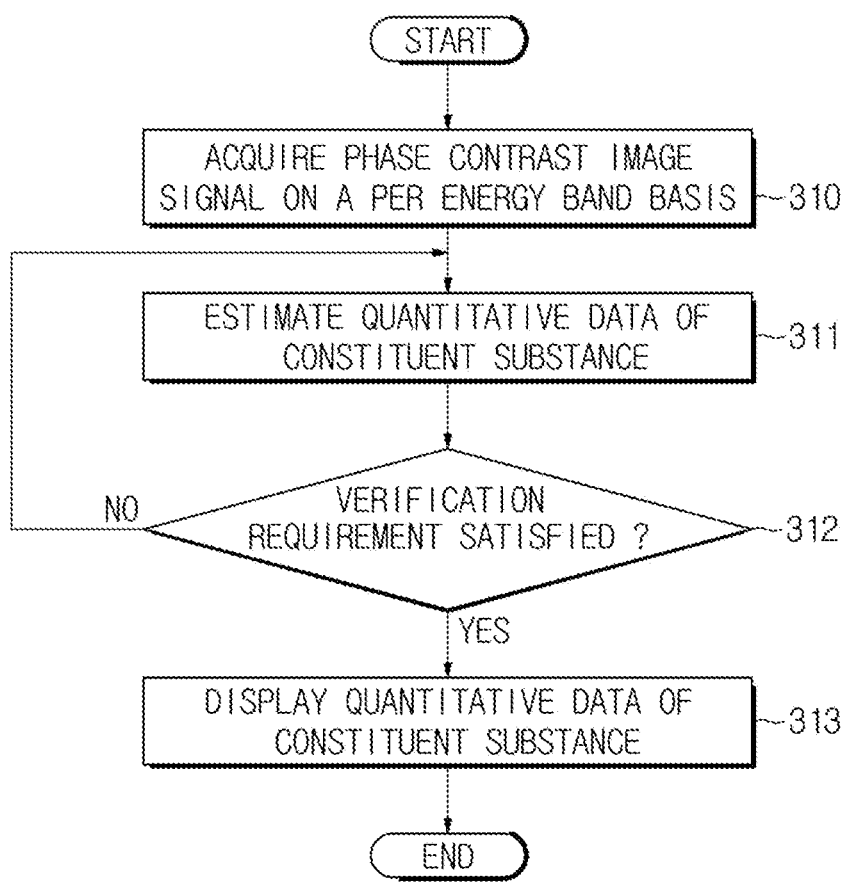
FIG. 17 is a flowchart showing a control method for the X-ray imaging apparatus according to an exemplary embodiment.

FIG. 17 is a flowchart showing a control method for the X-ray imaging apparatus according to an exemplary embodiment.

Referring to FIG. 17, first, phase contrast image signals on a per energy band basis with regard to the object are acquired (operation 310). The phase contrast image signals may be acquired by appropriately adjusting a distance between the object and the X-ray detector 120. To acquire the phase contrast image signals on a per energy band basis, the X-ray source 110 may emit X-rays having different energy bands respectively, or the X-ray detector 120 may separate X-rays into different energy bands.

Quantitative data regarding constituent substances of the object is estimated using the acquired phase contrast image signals (operation 311). The quantitative data regarding the constituent substances may be estimated on a per pixel basis or on a preset region basis. For example, approximate quantitative data may be calculated using a relationship between the phase contrast image signals and the quantitative data, and a regularization function may be iteratively applied to the approximate quantitative data to estimate thickness data having enhanced reliability.

After estimation of the quantitative data, the estimated quantitative data is verified. That is, it is judged whether the quantitative data satisfies a predefined verification requirement (operation 312). If the quantitative data does not satisfy the predefined verification requirement (No of Operation 312), the regularization function is again applied to estimate new thickness data. Examples of the verification requirement may include whether estimation is iteratively performed a predetermined number of times, or whether an error value of the quantitative data is equal to a predetermined reference value or less.

If the quantitative data satisfies the verification requirement (Yes of Operation 312), iterative estimation stops and the estimated quantitative data regarding the constituent substances is displayed to the user (operation 313). Although the estimated quantitative data may be displayed to the user, an image containing the estimated quantitative data may be displayed. Display of the image will be described in detail below.

The control method for the X-ray imaging apparatus enables acquisition of quantitative data regarding constituent substances of the object. In the following description, an exemplary embodiment in which thickness data among the quantitative data regarding the constituent substances is acquired will be described as an example.

Figure 18:
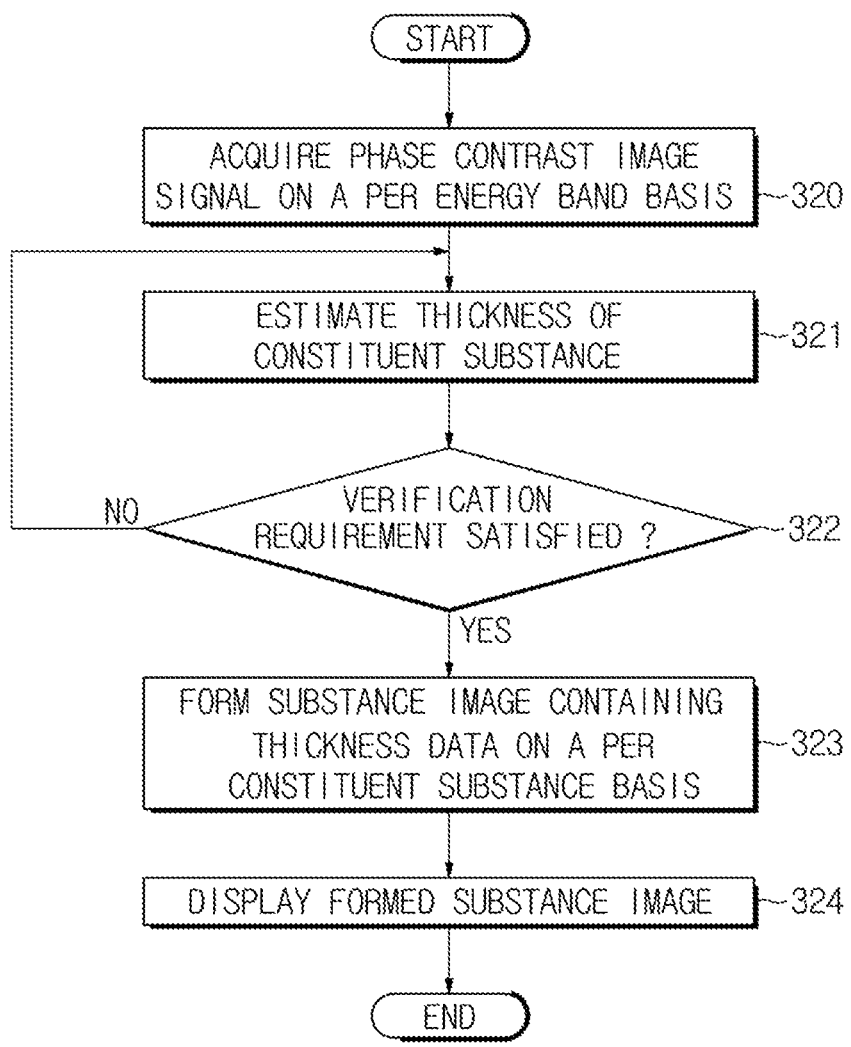
FIG. 18 is a flowchart showing an exemplary embodiment of a thickness data display method according to an exemplary embodiment.

FIG. 18 is a flowchart showing an exemplary embodiment of a thickness data display method.

Referring to FIG. 18, phase contrast image signals on a per energy band basis with regard to the object are acquired (operation 320), and thickness data regarding constituent substances of the object is estimated using the acquired phase contrast image signals (operation 321). Estimation of the thickness data may utilize the above Equation 1 to Equation 3.

It is judged whether the estimated thickness data satisfies a verification requirement (operation 322). If the estimated thickness data does not satisfy the verification requirement (No of Operation 322), the regularization function is again applied to estimate new thickness data regarding the constituent substances.

If the estimated thickness data satisfies the verification requirement (Yes of Operation 322), a substance image containing the thickness data on a per constituent substance basis is formed (operation 323). The estimation of the thickness data may be implemented on a per constituent substance basis, on a per pixel (corresponding to the constituent substance) basis, or on a per a predefined region basis. The substance image is an image of at least one constituent substance among the constituent substances of the object. In the case in which the substance image contains thickness data, brightness of each pixel corresponding to the constituent substance may correspond to thickness data regarding the corresponding pixel.

The formed substance image is displayed via the display (operation 324) and is supplied to the user.

Figure 19:
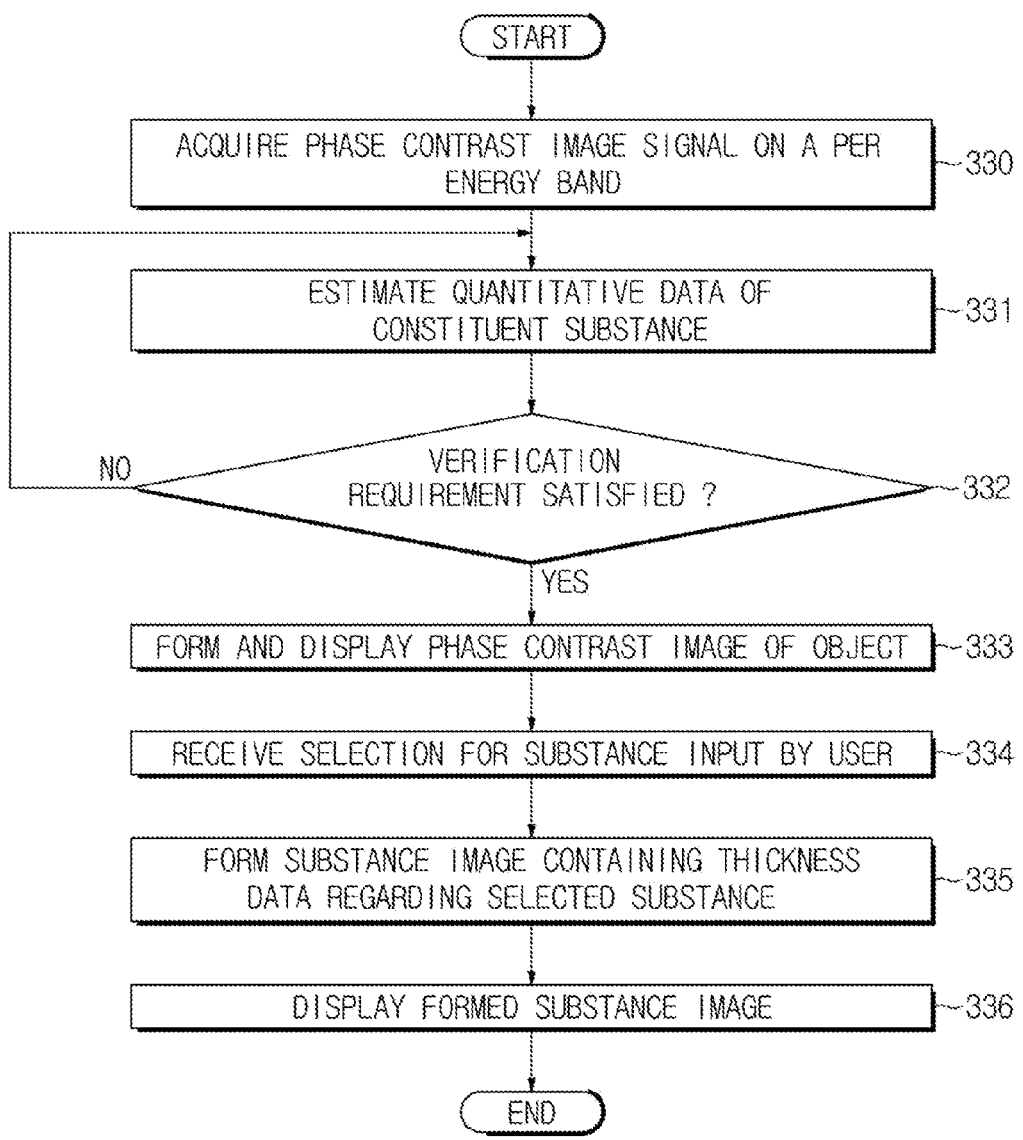
FIG. 19 is a flowchart showing a control method for the X-ray imaging apparatus that may allow a user to select a substance image according to an exemplary embodiment.

FIG. 19 is a flowchart showing a control method for the X-ray imaging apparatus that may allow the user to select a substance image.

Referring to FIG. 19, phase contrast image signals on a per energy band basis with regard to the object are acquired (operation 330), and thickness data regarding constituent substances of the object is estimated using the acquired phase contrast image signals (operation 331). It is judged whether the estimated thickness data satisfies a verification requirement (operation 332). If the estimated thickness data does not satisfy the verification requirement (No of Operation 322), a regularization function is applied to estimate new thickness data of the constituent substances. If the estimated thickness data satisfies the verification requirement (Yes or Operation 322), a phase contrast image of the object is formed and displayed (operation 333). The estimation of the thickness data may be implemented on a per a constituent substance basis, on a per pixel (corresponding to the constituent substance) basis, or on a per predefined region basis.

A method of forming the phase contrast image of the object has been described above, and, thus, a detailed description thereof will be omitted. Further, the control method for the X-ray imaging apparatus according to an exemplary embodiment does not limit the order of estimation of the thickness of constituent substances and formation of the phase contrast image of the object. Estimation of the thickness of constituent substances and formation of the phase contrast image of the object may be implemented at the same time, or formation of the phase contrast image of the object may be implemented first.

Once the phase contrast image of the object is displayed via the display 141, the user may select a target constituent substance of the object that the user wishes to know quantitative data thereof based on the displayed image. If the user inputs selection for the constituent substance (operation 334), a substance image containing thickness data regarding the selected constituent substance is formed (operation 335), and the formed substance image is displayed. As described above, to allow the substance image to contain the thickness data, brightness of each pixel may correspond to the thickness data regarding the corresponding pixel.

Figure 20:
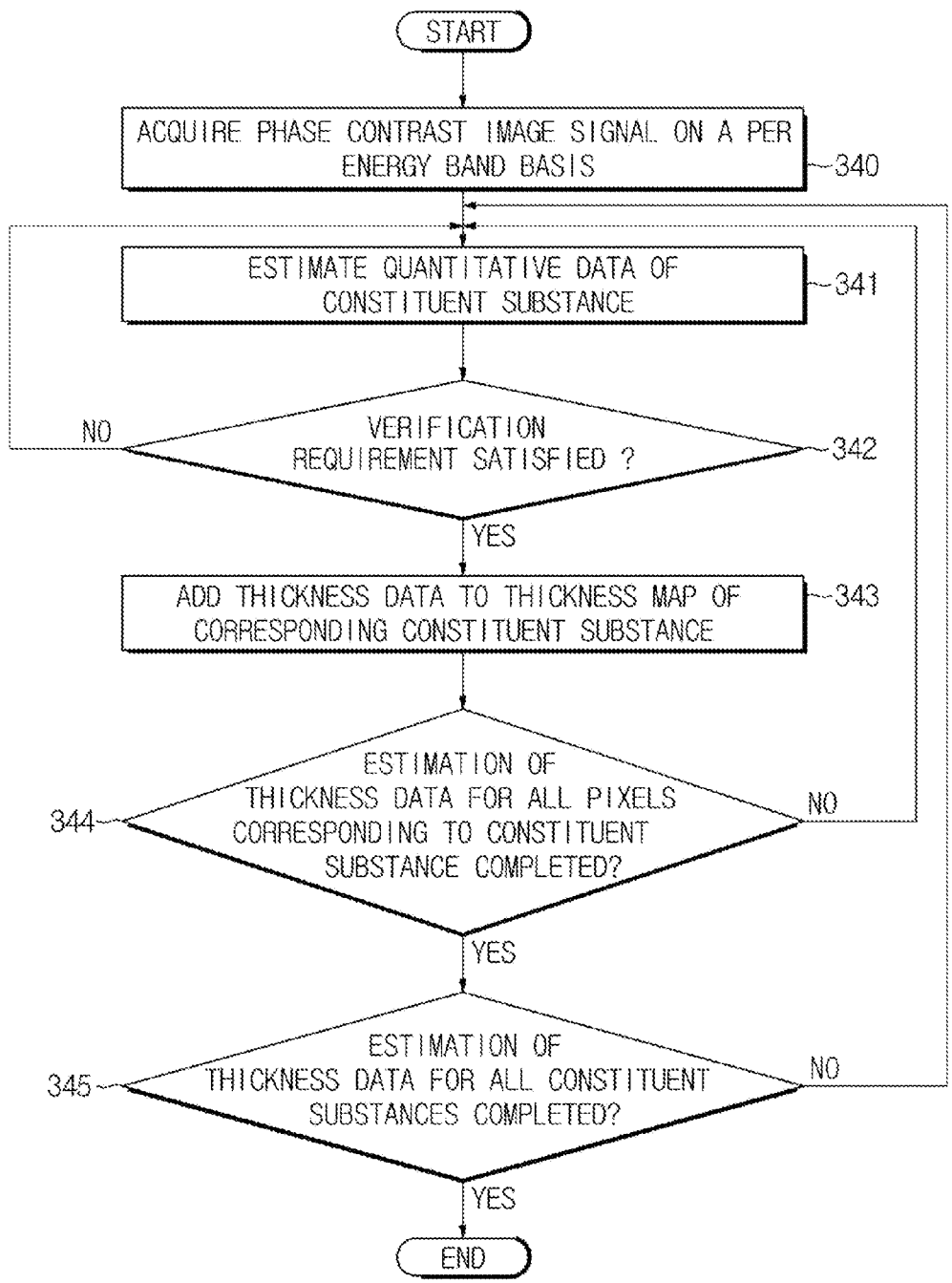
FIG. 20 is a flowchart showing generation of a thickness map on a per constituent substance basis according to an exemplary embodiment.

FIG. 20 is a flowchart showing generation of a thickness map on a per constituent substance basis in the control method for the X-ray imaging apparatus according to an exemplary embodiment.

Referring to FIG. 20, phase contrast image signals on a per energy band basis with regard to the object are acquired (operation 340), and thickness data regarding constituent substances of the object is estimated using the acquired phase contrast image signals (operation 341). Estimation of the thickness data may be implemented on a per constituent substance basis, on a per pixel (corresponding to the constituent substance) basis, or on a per predefined region basis. The present exemplary embodiment assumes that estimation of the thickness data is implemented on a per pixel basis.

It is judged whether the estimated thickness data satisfies a verification requirement (operation 342). If the estimated thickness data does not satisfy the verification requirement (No of Operation 342), a regularization function is applied to estimate new thickness data regarding the constituent substances.

If the estimated thickness data satisfies the verification requirement (Yes of Operation 342), finally estimated thickness data is acquired as final thickness data, and the acquired thickness data is added to a thickness map of the corresponding constituent substance (operation 343).

Then, it is judged whether estimation of the thickness data is completed with regard to all pixels corresponding to the constituent substance (operation 344). If estimation of the thickness data is completed with regard to only some of the pixels (No of Operation 344), estimation of the thickness data with regard to the remaining pixels is implemented and the resulting thickness data is added to the thickness data map.

If estimation of the thickness data is completed with regard to all the pixels (Yes of Operation 344), it is judged whether estimation of the thickness data is completed with regard to all constituent substances (operation 345). If estimation of the thickness data is completed with regard to only some of the constituent substances (No of Operation 345), estimation of the thickness data with regard to the remaining constituent substances is implemented to generate a thickness data map. If estimation of the thickness data is completed with regard to all of the constituent substances (Yes of Operation 345), generation of the thickness data map ends.

The control method for the X-ray imaging apparatus may utilize the aforementioned thickness map to display thickness data regarding each constituent substance or to form a substance image containing the thickness data.

FIGS. 18 and 19 illustrate formation of each substance image containing thickness data regarding each constituent substance. FIG. 21 is a flowchart showing generation of a single image containing thickness data on a per constituent substance basis in the control method for the X-ray imaging apparatus according to an exemplary embodiment.

Referring to FIG. 21, phase contrast image signals on a per energy band basis with regard to the object are acquired (operation 350), and thickness data on a per constituent substance basis is acquired using the acquired phase contrast image signals (operation 351). Acquisition of the thickness data may be implemented via iterative calculation and estimation.

A thickness map on a per constituent substance basis is generated using the acquired thickness data (operation 352), and a substance image containing thickness data on a per constituent substance basis is formed (operation 353). Formation of the substance image is described above.

Different color channels are mapped to a substance image on a per constituent substance basis (operation 354). For example, in the case of using an RGB color space, an R channel may be mapped to a constituent substance A, a G channel may be mapped to a constituent substance B, and a B channel may be mapped to a constituent substance C. Thickness data included in each substance image is represented by a mapped channel value. For example, in the image of the constituent substance A, a value of the R channel of each pixel may vary according to thickness data on a per pixel basis. This is equally applied to the other two images. There is no limit as to the color space used in the exemplary embodiments. For example, various other color spaces, such as a YCbCr color space, a CMY color space, a CMYK color space, etc., may be used.

The substance images, to which the color channels have been mapped, composed and displayed (operation 355). In the composite image, the respective constituent substances are distinguished by different colors, and thickness data regarding the respective constituent substances is represented as brightness.

Although thickness data has been described as quantitative data regarding the constituent substances in the above exemplary embodiments with regard to the control method for the X-ray imaging apparatus, the above description except for the aforementioned equations may be applied to other quantitative data.

As is apparent from the above description, according to an exemplary embodiment, it may be possible to estimate quantitative data regarding an object using phase contrast image signals corresponding to a plurality of different energy bands, thereby providing a user with the estimated data in various ways.

Although a few exemplary embodiments have been shown and described, exemplary embodiments are not limited thereto. It would be appreciated by those skilled in the art that changes may be made in these exemplary embodiments without departing from the principles and spirit of the disclosure, the scope of which is defined in the claims and their equivalents.

What is claimed is:
1. An X-ray imaging apparatus comprising:
an X-ray source configured to generate X-rays and emit the X-rays to an object;
an X-ray detector configured to detect X-rays having passed through the object for each of a plurality of different energy bands, and acquire phase contrast image signals on a per energy band basis, for each of the plurality of different energy bands;
a quantitative data acquirer configured to calculate approximate quantitative data of two or more constituent substances of the object using a relation between the phase contrast image signals on the per energy band basis and quantitative data of the constituent substances, and estimate quantitative data of the constituent substances by iteratively applying a regularization function to the approximate quantitative data; and a display configured to display an image generated based on the estimated quantitative data, wherein the quantitative data is related to a thickness of the constituent substances.

2. The apparatus according to claim 1, wherein the quantitative data acquirer determines whether the estimated quantitative data satisfies a verification criteria to verify reliability of the estimated quantitative data.

3. The apparatus according to claim 2, wherein the quantitative data acquirer determines the estimated quantitative data to be the quantitative data of the constituent substances if it is determined that the estimated quantitative data satisfies the verification criteria.

4. The apparatus according to claim 3, wherein the quantitative data acquirer estimates new quantitative data by applying again the regularization function to the estimated quantitative data if it is determined that the estimated quantitative data does not satisfy the verification criteria.

5. The apparatus according to claim 4, wherein the quantitative data acquirer determines that the estimated quantitative data satisfies the verification criteria when iterative application of the regularization function is repeated a preset number of times.

6. The apparatus according to claim 4, wherein the quantitative data acquirer determines that the estimated quantitative data satisfies the verification criteria when an error value of the estimated quantitative data is equal to a reference value or less.

7. The apparatus according to claim 4, wherein the quantitative data acquirer determines whether the estimated quantitative data satisfies the verification criteria whenever the regularization function is applied.

8. The apparatus according to claim 4, wherein the quantitative data acquirer determines whether the estimated quantitative data satisfies the verification criteria whenever application of the regularization function is repeated a preset number of times.

9. The apparatus according to claim 4, wherein the quantitative data acquirer acquires quantitative data of the constituent substances on a per region basis, and the region includes a single pixel.

10. The apparatus according to claim 9, further comprising a map generator that generates and stores a quantitative data map on a per constituent substance basis, the quantitative data map including the acquired quantitative data mapped on a per region basis.

11. The apparatus according to claim 9, further comprising a substance image former that forms a substance image containing the acquired quantitative data of the constituent substances.

12. The apparatus according to claim 11, wherein the substance image former causes brightness of each pixel corresponding to the constituent substances to have a value corresponding to the quantitative data of corresponding constituent substances.

13. The apparatus according to claim 11, further comprising an input unit that receives input selection for the constituent substances, wherein the substance image former forms the substance image of the selected constituent substances.

14. The apparatus according to claim 11, wherein a plurality of substance images is formed, and the substance image former causes different color channels to be mapped respectively to the plurality of substance images and composes the plurality of substance images to which the different color channels have been mapped.

15. A control method for an X-ray imaging apparatus, the method comprising:

acquiring phase contrast image signals of an object on a per energy band basis, by emitting X-rays to the object and detecting the X-rays having passed through the object for each of a plurality of different energy bands;

calculating approximate quantitative data of two or more constituent substances of the object using a relation between the phase contrast image signals on the per energy band basis and quantitative data of the constituent substances;

estimating quantitative data of the constituent substances by iteratively applying a regularization function to the approximate quantitative data; and displaying, on a display, an image generated based on the estimated quantitative data, wherein the quantitative data is related to a thickness of the constituent substances.

16. The method according to claim 15, further comprising determining whether the estimated quantitative data satisfies a verification criteria to verify reliability of the estimated quantitative data.

17. The method according to claim 16, further comprising determining the estimated quantitative data to be the quantitative data of the constituent substances if it is determined that the estimated quantitative data satisfies the verification criteria.

18. The method according to claim 17, further comprising estimating new quantitative data by applying again the regularization function to the estimated quantitative data if it is determined that the estimated quantitative data does not satisfy the verification criteria.

19. The apparatus according to claim 1, wherein the X-ray source is configured to generate spatially coherent X-rays.

* * * * *